US011268127B2

(12) United States Patent
Lopez et al.

(10) Patent No.: US 11,268,127 B2
(45) Date of Patent: Mar. 8, 2022

(54) SYSTEMS AND DEVICES FOR PROTEASE DETECTION BASED ON ENGINEERED POLYMERS AND BIOPOLYMERS AND METHODS OF USE

(71) Applicants: Gabriel P. Lopez, Durham, NC (US); Ashutosh Chilkoti, Durham, NC (US); Ali Ghoorchian, Durham, NC (US); Felipe Garcia Quiroz, Durham, NC (US); Duke University, Durham, NC (US)

(72) Inventors: Gabriel P. Lopez, Durham, NC (US); Ashutosh Chilkoti, Durham, NC (US); Ali Ghoorchian, Durham, NC (US); Felipe Garcia Quiroz, Durham, NC (US)

(73) Assignee: Duke University, Durham, NC (US)

( * ) Notice: Subject to any disclaimer, the term of this patent is extended or adjusted under 35 U.S.C. 154(b) by 753 days.

(21) Appl. No.: 15/116,750

(22) PCT Filed: Feb. 4, 2015

(86) PCT No.: PCT/US2015/014514
§ 371 (c)(1),
(2) Date: Aug. 4, 2016

(87) PCT Pub. No.: WO2015/120091
PCT Pub. Date: Aug. 13, 2015

(65) Prior Publication Data
US 2016/0348147 A1 Dec. 1, 2016

Related U.S. Application Data

(60) Provisional application No. 61/935,479, filed on Feb. 4, 2014.

(51) Int. Cl.
*C12Q 1/37* (2006.01)
*G01N 33/573* (2006.01)

(52) U.S. Cl.
CPC ............. *C12Q 1/37* (2013.01); *G01N 33/573* (2013.01)

(58) Field of Classification Search
CPC ......................... C07K 2319/50; C07K 14/78
See application file for complete search history.

(56) References Cited

U.S. PATENT DOCUMENTS

| 5,169,933 A | 12/1992 | Anderson et al. |
| 2009/0087842 A1 | 4/2009 | Ohtsuka et al. |
| 2013/0143802 A1 | 6/2013 | Chilkoti |
| 2013/0330335 A1 | 12/2013 | Bremel et al. |

FOREIGN PATENT DOCUMENTS

| WO | 2012171024 A2 | 12/2012 |
| WO | WO-2015120091 A1 | 8/2015 |

OTHER PUBLICATIONS

Trent et al., "Structural properties of soluble peptide amphiphile micelles", Soft Matter, 2011, 9572-9582 (Year: 2011).*
International Preliminary Report on Patentability received in PCT/US2015/014514 dated Aug. 18, 2016.
International Search Report received in PCT/US15/14541 dated May 27, 2015.
Written Opinion received in PCT/US15/14514 dated May 27, 2015.
King et al., "Peptidylarginine Deiminases and Protein Deimination in Skin Physiopathology, Psoriasis—A Systemic Disease," (Mar. 2012). Dr. Jose O' Daly (Ed.), chapter 6, pp. 117-132, p. 117, para 1, p. 119, para 1, Figure 1.
Garanger, Elisabeth, et al., "Structural Evolution of a Stimulus-Responsive Diblock Polypeptide Micelle by Temperature Tunable Compaction of its Core", Macromolecules, American Chemical Society, 2015, 48 (18), 6617-6627.
Hassouneh, Wafa, et al., "Elastin-like Polypeptide Diblock Copolymers Self-Assemble into Weak Micelles", Macromolecules 2015, 48, (Jun. 11, 2015), 4183-4195.
Kracke, Bettina, et al., "Thermoswitchable Nanoparticles Based on Elastin-like Polypeptides", Macromolecules 2015, 48, (Aug. 13, 2015), 5868-5877.
Le, Duc H.T., et al., "Elastin-like polypeptides as building motifs toward designing functional nanobiomaterials", Mol. Syst. Des. Eng., 2019, 4, 545-565.
Ro, Jang-Won, et al., "Characterization of Amphiphilic Elastin-like Polypeptide (ELP) Block Copolymers as Drug Delivery Carriers", Biotechnology and Bioprocess Engineering 23, (2018), 627-633.
Saha, Soumen, et al., "Engineering the Architecture of Elastin-Like Polypeptides: From Unimers to Hierarchical Self-Assembly", Advanced Therapeutics 2020, 3, 1900154, 23 pgs.
Ghoorchian, Ali, et al., "A Simple Assay for Proteases Based on Aggregation of Stimulus-Responsive Polypeptides", Supporting Information, 9 pgs.
Ghoorchian, Ali, et al., "Simple Assay for Proteases Based on Aggregation of Stimulus-Responsive Polypeptides", Analytical Chemistry 86, 12, (May 16, 2014), 6103-6110.

* cited by examiner

*Primary Examiner* — Lianko G Garyu
(74) *Attorney, Agent, or Firm* — Schwegman Lundberg & Woessner, P.A.

(57) ABSTRACT

The presently disclosed subject matter relates to modular peptide-substrate protease assays, in particular low cost and reliable methodology for measurement of protease and other enzyme activity that may be detected by optical turbidimetry or visual observation. The presently disclosed subject matter also relates to methods of using the disclosed assays within methods of detecting and monitoring diseases, methods of drug discovery, as well as in detection devices and systems.

36 Claims, 24 Drawing Sheets
Specification includes a Sequence Listing.

B

C

SEQUENCE LISTING

```
<160> NUMBER OF SEQ ID NOS: 23

<210> SEQ ID NO 1
<211> LENGTH: 30
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (2)..(6)
<223> OTHER INFORMATION: Repeats 60 times

<400> SEQUENCE: 1

Met Gly Val Gly Val Pro Gly Asp Gly Gln Val Pro Met Ser Met Arg
1               5                   10                  15

Gly Gly Asp Asp Glu Gly Gln Gln Asp Asp Glu Glu Gly Tyr
            20                  25                  30

<210> SEQ ID NO 2
<211> LENGTH: 49
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (11)..(15)
<223> OTHER INFORMATION: Repeats 60 times
<220> FEATURE:
<221> NAME/KEY: REPEAT
<222> LOCATION: (38)..(47)
<223> OTHER INFORMATION: Repeats 30 times

<400> SEQUENCE: 2
```

```
Met Ser Lys Gly Pro Gly Trp Gly Val Gly Val Pro Gly Val Gly Gly
1               5                   10                  15

Asp Gly Gln Val Pro Met Ser Met Arg Gly Gly Asp Glu Gly Gln
            20                  25                  30

Gln Asp Asp Glu Glu Val Pro Gly Ala Gly Val Pro Gly Gly Tyr
        35                  40                  45

Gly

<210> SEQ ID NO 3
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 3

Gly Asp Gly Gln Val Pro Met Ser Met Arg Gly Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (1)..(5)
<223> OTHER INFORMATION: Repeats 60 times

<400> SEQUENCE: 4

Val Pro Gly Val Gly
1               5

<210> SEQ ID NO 5
<211> LENGTH: 10
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (1)..(10)
<223> OTHER INFORMATION: Repeats 30 times

<400> SEQUENCE: 5

Val Pro Gly Ala Gly Val Pro Gly Gly Gly
1               5                   10

<210> SEQ ID NO 6
<211> LENGTH: 26
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (2)..(6)
<223> OTHER INFORMATION: Repeats 60 times

<400> SEQUENCE: 6

Met Gly Val Gly Val Pro Gly Asp Gly Gln Ser Ser Ile Tyr Ser Gln
1               5                   10                  15

Thr Glu Glu Gln Gln Asp Asp Glu Glu Gly
            20                  25
```

<210> SEQ ID NO 7
<211> LENGTH: 33
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (2)..(9)
<223> OTHER INFORMATION: Repeats 40 times

<400> SEQUENCE: 7

Met Tyr Pro Ser Asp Gly Arg Gly Gln Tyr Gly Asp Gly Gln Val Pro
1               5                   10                  15

Met Ser Met Arg Gly Gly Asp Glu Gly Gln Gln Asp Asp Glu Glu Gly
            20                  25                  30

Tyr

<210> SEQ ID NO 8
<211> LENGTH: 17
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (1)..(17)
<223> OTHER INFORMATION: Repeats y times
<220> FEATURE:
<221> NAME/KEY: REPEAT
<222> LOCATION: (13)..(17)
<223> OTHER INFORMATION: Repeats x times

<400> SEQUENCE: 8

Gly Ser Gly Arg Gly Lys Gly Gly Lys Gly Leu Gly Val Pro Gly Val
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (1)..(17)
<223> OTHER INFORMATION: Repeats y times
<220> FEATURE:
<221> NAME/KEY: MISC_FEATURE
<222> LOCATION: (4)..(4)
<223> OTHER INFORMATION: X = Citrulline
<220> FEATURE:
<221> NAME/KEY: REPEAT
<222> LOCATION: (13)..(17)
<223> OTHER INFORMATION: Repeats x times

<400> SEQUENCE: 9

Gly Ser Gly Xaa Gly Lys Gly Gly Lys Gly Leu Gly Val Pro Gly Val
1               5                   10                  15

Gly

<210> SEQ ID NO 10
<211> LENGTH: 11
<212> TYPE: PRT
<213> ORGANISM: Artificial Sequence
<220> FEATURE:
<223> OTHER INFORMATION: Recombinant polypeptide

```
<400> SEQUENCE: 10

Asp Gly Gln Val Pro Met Ser Met Arg Gly Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Recombinant polypeptide

<400> SEQUENCE: 11

Asp Glu Gly Gln Gln Asp Asp Glu Glu Gly Tyr
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 12

Val Pro Met Ser Met Arg Gly Gly
1               5

<210> SEQ ID NO 13
<211> LENGTH: 11
<212> TYPE: PRT
<213> ORGANISM: Artificial Sequence
<220> FEATURE:
<223> OTHER INFORMATION: Recombinant polypeptide

<400> SEQUENCE: 13

Ser Ser Ile Tyr Ser Gln Thr Glu Glu Gln Gln
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Recombinant polypeptide

<400> SEQUENCE: 14

Lys Pro Gly Leu Lys Arg
1               5

<210> SEQ ID NO 15
<211> LENGTH: 4
<212> TYPE: PRT
<213> ORGANISM: Artificial Sequence
<220> FEATURE:
<223> OTHER INFORMATION: Recombinant polypeptide

<400> SEQUENCE: 15

Leu Lys Lys Arg
1

<210> SEQ ID NO 16
<211> LENGTH: 6
<212> TYPE: PRT
<213> ORGANISM: Artificial Sequence
<220> FEATURE:
<223> OTHER INFORMATION: Recombinant polypeptide
```

```
<400> SEQUENCE: 16

Leu Gln Tyr Thr Lys Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Recombinant polypeptide

<400> SEQUENCE: 17

Lys Lys Arg Gly Asp Ala Lys
1               5

<210> SEQ ID NO 18
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 18

Glu Ala Glu Ala Ile Tyr Ala Ala Pro Gly Asp Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 19

Gly Asp Gln Asp Tyr Leu Ser Leu Asp Lys
1               5                   10

<210> SEQ ID NO 20
<211> LENGTH: 33
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (2)..(9)
<223> OTHER INFORMATION: Repeats 20 times

<400> SEQUENCE: 20

Met Tyr Pro Ser Asp Gly Arg Gly Gln Tyr Gly Asp Gly Gln Val Pro
1               5                   10                  15

Met Ser Met Arg Gly Gly Asp Glu Gly Gln Gln Asp Asp Glu Glu Gly
                20                  25                  30

Tyr

<210> SEQ ID NO 21
<211> LENGTH: 32
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (2)..(8)
<223> OTHER INFORMATION: Repeats 16 times

<400> SEQUENCE: 21
```

```
Met Tyr Gly Arg Gly Asp Ser Ala Tyr Gly Asp Gly Gln Val Pro Met
1               5                   10                  15

Ser Met Arg Gly Gly Asp Glu Gly Gln Gln Asp Asp Glu Glu Gly Tyr
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (2)..(7)
<223> OTHER INFORMATION: Repeats 24 times

<400> SEQUENCE: 22

Met Tyr Gly Arg Gly Asp Ser Ala Tyr Gly Asp Gly Gln Val Pro Met
1               5                   10                  15

Ser Met Arg Gly Gly Asp Glu Gly Gln Gln Asp Asp Glu Glu Gly Tyr
            20                  25                  30

<210> SEQ ID NO 23
<211> LENGTH: 5
<212> TYPE: PRT
<213> ORGANISM: Artificial Sequence
<220> FEATURE:
<223> OTHER INFORMATION: Recombinant polypeptide
<220> FEATURE:
<221> NAME/KEY: REPEAT
<222> LOCATION: (1)..(5)
<223> OTHER INFORMATION: Repeats 60 times

<400> SEQUENCE: 23

Gly Val Gly Val Pro
1               5
```

SYSTEMS AND DEVICES FOR PROTEASE DETECTION BASED ON ENGINEERED POLYMERS AND BIOPOLYMERS AND METHODS OF USE

CROSS-REFERENCE TO RELATED APPLICATIONS

This application is a 35 U.S.C. 371 application of PCT International Patent Application No. PCT/US2015/014514, filed Feb. 4, 2015, which claims the benefit of U.S. Provisional Application No. 61/935,479, filed Feb. 4, 2014, which is incorporated herein by reference in its entirety.

FEDERALLY SPONSORED RESEARCH OR DEVELOPMENT

This invention was made in part using Government Support under Federal Grant No. DMR-1121107 awarded by the National Science Foundation. Accordingly, the Federal Government has certain rights to this invention.

TECHNICAL FIELD

Embodiments described herein relate to protease detection assays. More particularly, embodiments described herein relate to systems, devices, and methods for protease detection using engineered polymers and biopolymers.

BACKGROUND

The concentration and activity of proteases are precisely regulated in vivo and disruption of this homeostasis is linked to a number of pathological disorders, ranging from inflammatory and cardiovascular disease to cancer and neurological abnormalities (Turk, B. Nature Reviews Drug Discovery 2006, 5, 785-799). Proteases are also key molecular actors in the initiation and progression of many infectious diseases. The ability to detect changes in protease activity is thus powerful for diagnosing protease-related diseases, as well as for discovering new drugs against these diseases. Today, nearly 10% of commercial therapeutics target proteases (Drag, M. & Salvesen, G. S. Nature Reviews Drug Discovery 2010, 9, 690-701; Zheng, C. J. et al., Pharmacological Reviews 2006, 58, 259-279). Matrix metalloproteinases (MMPs) are a therapeutically important class of proteases that encompass a group of 24 zinc-dependent endopeptidases that collectively cleave various structural components of the extracellular matrix (ECM) (Coussens, L. M. et al., Science 2002, 295, 2387-2392; Zitka, O. et al., Current Medicinal Chemistry 2010, 17, 3751-3768). They are involved in tissue remodeling, cell migration and a variety of normal and pathological conditions (McCawley, L. J. & Matrisian, L. M. Current Opinion in Cell Biology 2001, 13, 534-540). In normal tissues at homeostasis, the expression levels of MMPs are usually low and are balanced with MMP inhibitors, but they can very quickly elevate during normal or pathological remodeling of tissues, including processes associated with metastastic cancer (Sato, H. et al., Nature 1994, 370, 61-65).

The expression profile of MMPs varies considerably from one MMP to another and from one cancer to another, and monitoring their concentration and activity over time can be an effective way of monitoring the state of the disease (Decock, J. et al., Bmc Cancer 2008, 8, 77; Nikkola, J. et al., Clinical Cancer Research 2005, 11, 5158-5166). For instance, high levels of MMP-9 after treatment of patients with melanoma correlate with poor survival rate, and in metastatic melanoma patients high levels of MMP-1 (>30 ng/mL) in blood serum correlate with a faster progression of the disease (Nikkola, J. et al., Clinical Cancer Research 2005, 11, 5158-5166). MMP-1 has also been associated with a number of other cancers, including early stage lung cancer (Hart, K. et al., Lung Cancer 2011, 71, 123-129), breast cancer (Decock, J. et al., Bmc Cancer 2008, 8, 77), and metastatic colorectal cancer (Sunami, E. et al., The oncologist 2000, 5, 108-114). There are also reports of high serum levels of MMP-1 in patients with certain inflammatory and cardiovascular diseases (Schwartzkopff, B. et al., European Journal of Heart Failure 2002, 4, 439-444). The extent of involvement of MMPs in various stages of different diseases is a clear indication that they may be useful as diagnostic biomarkers.

There are many assays available for detection and quantification of proteases and their activities, which can be broadly categorized into immunoassays and enzymatic assays (Krizkova, S. et al., Trac-Trends in Analytical Chemistry 2011, 30, 1819-1832; Lombard, C. et al., Chemical Communications 2009, 34-46). Immunoassays have been used extensively for applications ranging from drug discovery (Paganetti, P. et al., Chembiochem 2009, 10, 1678-1688; Roda, A. et al., Trends in Biotechnology 2004, 22, 295-303) to in vitro diagnosis (Blackburn, G. F. et al., Clinical Chemistry 1991, 37, 1534-1539; Chin, C. D. et al., Nature Medicine 2011, 17, 1015-U1138; Rusling, J. F. Analytical Chemistry 2013, 85, 5304-5310; Biagini, R. E. et al., Clinical and Diagnostic Laboratory Immunology 2004, 11, 50-55). Enzymatic assays have also been used in drug discovery (Tian, H. et al., British Journal of Pharmacology 2007, 150, 321-334; Wang, M. et al., Analytical Chemistry 2009, 81, 4444-4449), and clinical and point-of-care diagnostics (Manafi, M. et al., Microbiological Reviews 1991, 55, 335-348; Tsai, T. T. et al., Science and Technology of Advanced Materials 2013, 14, 044404).

Many different kinds of substrates have been used in enzymatic assays for proteases, including native proteins (Manicourt, D. H. & Lefebvre, V. Analytical Biochemistry 1993, 215, 171-179), short peptide sequences (Bolduc, O. R. et al., Analytical Chemistry 2010, 82, 3699-3706), and assembled peptides (Lauer-Fields, J. L. et al., Journal of Biological Chemistry 2000, 275, 13282-13290). Peptide sequences are generally easier to design and modify and as a result, many assays use short peptides, which, upon cleavage by a protease, cause a detectable change in the substrate molecule, the rate of which can be correlated to the enzyme concentration in the solution. Assays based on protease-sensitive peptides are finding many uses including early cancer detection (Hart, K. et al., Lung Cancer 2011, 71, 123-129; Harmsma, M. et al., Biochimica Et Biophysica Acta-Reviews on Cancer 2013, 1836, 255-272), discovery of inhibitors against infectious diseases like West Nile virus (Chappell, K. J. et al., Journal of Biological Chemistry 2006, 281, 38448-38458), HIV (Kilby, J. M. et al., Nature Medicine 1998, 4, 1302-1307), and Dengue (Ekonomiuk, D. et al., Plos Neglected Tropical Diseases 2009, 3, e356), understanding regulatory mechanism in cell growth (Blume-Jensen, P. & Hunter, T. Nature 2001, 411, 355-365), and developing peptidases as therapeutics (Francis, S. E. et al., Annual Review of Microbiology 1997, 51, 97-123).

Regardless of the type of substrate that is used, separation, detection, and quantification of products after enzymatic reaction are often challenging and necessitate expensive or sophisticated methods (e.g., flourimetry, chromatography, and calorimetry) implemented by dedicated technicians)

(Goddard, J. P. & Reymond, J. L. *Trends in Biotechnology* 2004, 22, 363-370). The most practical and widely used assays are based on substrates that release fluorescent products as a result of a reaction, or based on precipitation of a substrate (Reymond, J. L. et al., *Chemical Communications* 2009, 34-46). Both of these assay types allow facile detection, but between the two, precipitation assays generally have the advantage of simpler detection over fluorescence assays. On the other hand, precipitation methods usually need a second component, like an antibody, to induce aggregation, and they generally lack the sensitivity of fluorimetric methods (Reymond, J. L. et al., *Chemical Communications* 2009, 34-46). Consequently, an assay that can combine the simplicity of precipitation assays and high sensitivity would be highly desirable.

SUMMARY

In one aspect, the presently disclosed subject matter provides a method for detecting protease activity in a sample comprising the steps of: a) contacting the sample with amphiphilic fusion polypeptides, wherein each of the fusion polypeptides comprise a hydrophobic domain and a hydrophilic domain separated by a protease substrate domain, wherein the fusion polypeptides self-assemble into micelles, and further wherein the micelles comprise coronae comprising the protease substrate domains; b) providing conditions in which protease present in the sample will cleave the protease substrate domains, whereby the hydrophobic domains of the micelles aggregate into particles at a detectable aggregation rate; and c) detecting the aggregation rate of particles in the sample; wherein the aggregation rate of particles in the sample is positively correlated to the protease activity in the sample. In particular aspects, the aggregation rate of particles may be detected by optical turbidimetry or visual observation.

In another aspect, the presently disclosed subject matter provides a method for detecting protease activity in a sample comprising the steps of: a) contacting the sample with amphiphilic fusion polypeptides, wherein each of the fusion polypeptides comprise a hydrophobic phase transition domain and a hydrophilic domain separated by a protease substrate domain, wherein the fusion polypeptides self-assemble into micelles in response to a stimulus that triggers phase transition of the phase transition domains, and further wherein the micelles comprise coronae comprising the protease substrate domains; b) presenting the stimulus to the fusion polypeptides, whereby the fusion polypeptides self-assemble into micelles; c) providing conditions in which protease present in the sample will cleave the protease substrate domains, whereby the hydrophobic phase transition domains of the micelles aggregate into particles at a detectable aggregation rate; and d) detecting the aggregation rate of particles in the sample; wherein the aggregation rate of particles in the sample is positively correlated to the protease activity in the sample. In a particular aspect, the stimulus is temperature. In another aspect, the hydrophobic phase transition domains display lower critical solution temperature (LCST) behavior. In yet other aspects, the hydrophobic phase transition domains comprise elastin-like polypeptides and/or the hydrophilic domains comprise anionic peptides. In further aspects, the protease substrate domains comprise a cleavage site for a protease selected from the group consisting of a serine protease, a threonine protease, a cysteine protease, an asparatic protease, a glutamic protease, and a metalloproteinase. In particular aspects, the aggregation rate of particles may be detected by optical turbidimetry or visual observation.

In another aspect, a method for detecting protease activity in a sample is provided comprising the steps of: a) contacting the sample with fusion polypeptides, wherein each of the fusion polypeptides comprise a phase transition domain, a protease substrate domain and an optional hydrophilic or a hydrophobic domain, wherein the phase transition domains display upper critical solution temperature (UCST) behavior; b) providing conditions in which protease present in the sample will cleave the protease substrate domains, whereby the phase transition domains aggregate into particles at a detectable aggregation rate; and c) detecting the aggregation rate of particles in the sample; wherein the aggregation rate of particles in the sample is positively correlated to the protease concentration in the sample. In further aspects, the hydrophilic domains comprise anionic peptides and/or the protease substrate domains comprise a cleavage site for a protease selected from the group consisting of a serine protease, a threonine protease, a cysteine protease, an asparatic protease, a glutamic protease, and a metalloproteinase. In particular aspects, the aggregation rate of particles may be detected by optical turbidimetry or visual observation.

In another aspect, a method for detecting enzyme activity in a sample is provided comprising the steps of: a) contacting the sample with fusion polypeptides, wherein each of the fusion polypeptides comprise a phase transition domain and an enzyme substrate domain; b) providing conditions in which enzyme present in the sample will bind to and modify the enzyme substrate domains, whereby a transition temperature for the fusion polypeptides is increased above the temperature of the sample, and further wherein the fusion polypeptides aggregate into particles at a detectable aggregation rate; and c) detecting the aggregation rate of particles in the sample; wherein the aggregation rate of particles in the sample is positively correlated to the enzyme activity in the sample. In a particular aspect, the enzyme is a Protein arginine deiminase (PAD). In particular aspects, the aggregation rate of particles may be detected by optical turbidimetry or visual observation.

In another aspect, a method of predicting or diagnosing a disease in a subject is provided comprising: a) obtaining a biological sample from the subject; b) detecting the activity of an enzyme in the biological sample using any of the methods for detecting enzyme activity described herein; and c) comparing the activity of the enzyme in the biological sample to the activity of the enzyme from a control sample from the subject or a control sample from subjects who do not have the disease; wherein a significant difference between the activity of the enzyme in the biological sample and the control sample is indicative that the subject has or is susceptible to developing the disease. In particular aspects, the disease is selected from the group consisting of an infectious disease, an inflammatory disease, a cardiovascular disease, and a cancer. In further aspects, the enzyme is a protease, particularly wherein the protease is selected from the group consisting of a serine protease, a threonine protease, a cysteine protease, an asparatic protease, a glutamic protease, and a metalloproteinase.

In another aspect, a method of monitoring the progression or recurrence of a disease in a subject is provided comprising: a) obtaining a biological sample from the subject; b) detecting the activity of an enzyme in the biological sample using any of the methods for detecting enzyme activity described herein; and c) comparing the activity of the enzyme in the biological sample to the activity of the enzyme from a control sample from the subject or a control sample from subjects who do not have the disease; wherein a significant difference between the activity of the enzyme in the biological sample and the control sample is indicative of the progression or recurrence of the disease in the subject. In particular aspects, the disease is selected from the group consisting of an infectious disease, an inflammatory disease, a cardiovascular disease, and a cancer. In further aspects, the enzyme is a protease, particularly wherein the protease is selected from the group consisting of a serine protease, a threonine protease, a cysteine protease, an asparatic protease, a glutamic protease, and a metalloproteinase.

In another aspect, a method for determining the efficacy of a therapeutic treatment for a disease in a subject undergoing the treatment is provided comprising: a) obtaining a biological sample from the subject; b) detecting the activity of an enzyme in the biological sample using any of the methods for detecting enzyme activity described herein; and c) comparing the activity of the enzyme in the biological sample to the activity of the enzyme from a control sample from the subject or a control sample from subjects who do not have the disease; wherein a significant difference between the activity of the enzyme in the biological sample and the control sample is indicative of the efficacy of the therapeutic treatment of the disease in the subject. In particular aspects, the disease is selected from the group consisting of an infectious disease, an inflammatory disease, a cardiovascular disease, and a cancer. In further aspects, the enzyme is a protease, particularly wherein the protease is selected from the group consisting of a serine protease, a threonine protease, a cysteine protease, an asparatic protease, a glutamic protease, and a metalloproteinase.

In another aspect, a method of identifying an agent that inhibits the activity of an enzyme is provided comprising: a) detecting the activity of an enzyme in a sample using any of the methods for detecting enzyme activity described herein; b) contacting the sample with a candidate agent; and c) comparing the activity of the enzyme in the sample after contact with the candidate agent to the activity of the enzyme in the sample before contact with the candidate agent; wherein a significant decrease in the activity of the enzyme in the sample after contact with the candidate agent compared to the activity of the enzyme in the sample before contact with the candidate agent is indicative that the candidate agent is an agent that inhibits the activity of the enzyme. In a particular aspect, the enzyme is a protease, more particularly a protease is selected from the group consisting of a serine protease, a threonine protease, a cysteine protease, an asparatic protease, a glutamic protease, and a metalloproteinase.

In other aspects, a device is provided designed to perform any of the method steps of any one of the methods described herein. In a further aspect, a computer readable medium is provided that is programmed to cause a device to perform any of the method steps of the methods described herein. In a further aspect, a system is provided comprising a device coupled to and controlled by a computer programmed to cause the device to perform any of the method steps of any one of the methods described herein.

BRIEF DESCRIPTION OF THE DRAWINGS

The foregoing summary, as well as the following detailed description of various embodiments, is better understood when read in conjunction with the drawings provided herein. For the purposes of illustration, there is shown in the drawings exemplary embodiments; however, the presently disclosed subject matter is not limited to the specific methods and instrumentalities disclosed.

DETAILED DESCRIPTION

Figure 1:
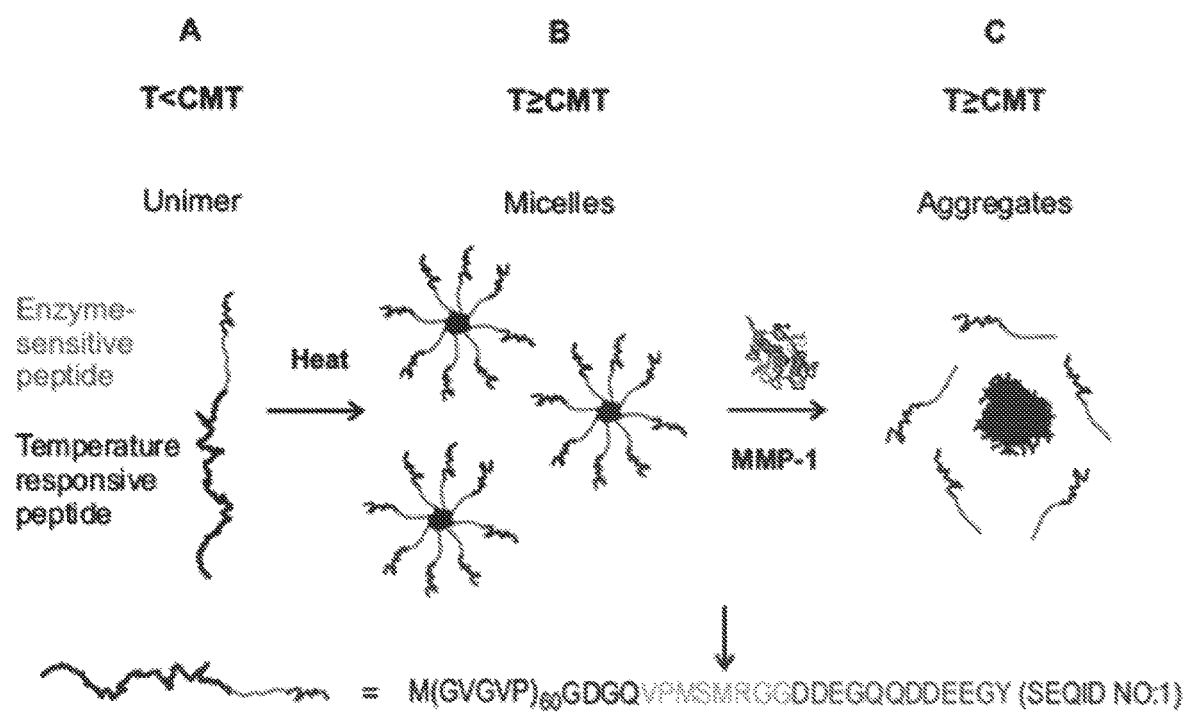
FIG. 1 shows the sequence of the engineered, stimuli-responsive polypeptide (unimer, herein referred to as ELP-substrate fusion), schematic depiction of its micellization above its critical micellization temperature (CMT), and subsequent aggregation of the ELP after incubation with the enzyme, MMP-1 at a temperature >CMT.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Unless defined otherwise, all technical and scientific terms used herein have the meaning commonly understood by a person skilled in the art to which this invention belongs.

Modular Peptide-Substrate Protease Assay

Unregulated changes in protease activity are linked to many diseases including cancer, infectious, inflammatory, and even cardiovascular diseases. The concentration and activity of proteases are precisely regulated in vivo and disruption of this homeostasis is linked to a number of pathological disorders, from inflammatory and cardiovascular disease to cancer and neurological abnormalities. The ability to detect changes in protease activity is thus a powerful potential means for diagnosing protease-related diseases, as well as for discovering new drugs against these maladies.

The presently disclosed subject matter relates to the development of a protease assay system that is adaptable to different proteases through simple changes to a modular peptide-substrate design. The presently disclosed protease assay system utilizes engineered recombinant polypeptides to provide a simple, low cost and yet reliable methodology for measurement of protease function that can be easily performed and that does not require complex instrumentation or a complex protocol. The approach uses modular polypeptide amphiphiles that self-assemble into micelles above a critical micellization temperature (CMT) and present a protease substrate peptide on their corona that is accessible to proteases in solution. The cleavage of the protease-sensitive peptide on the corona of the micelles by the protease abrogates the amphiphilicity of the polypeptide, which triggers a phase transition of the remainder of the polypeptide into micron-size aggregates that can be easily detected by optical turbidimetry. This assay is simple to carry out, provides direct optical read-out of protease concentration, and has a limit-of-detection and dynamic range that is compatible with the range of blood concentration of specific proteases that are diagnostic of different diseases.

The flexible nature of this system allows for a variety of ways to design and construct the system. Examples of such systems for detection of MMP-1 are presented elsewhere herein. However, there are many other approaches that can be taken to modify the design of this system and still use the same principles for the detection and quantification of proteases and other enzymes. The modular design of the system can be utilized to easily change the molecular design of the peptide or polymer to make the system compatible to different conditions.

Use of Other Protease-Sensitive Peptides.

In general the proteases are broadly categorized into different groups, including serine protease, threonine protease, cysteine protease, asparatic protease, glutamic protease, and metalloproteinase. Enzymes in any of these protease families can potentially be used as a target enzyme for the presently disclosed assay. This can be achieved by choosing the corresponding enzyme-sensitive peptide for each system. The reaction conditions and buffer compositions for the enzymatic reactions can be adjusted accordingly to allow detection of the changes in optical density as a function of time and quantify the enzyme concentration accordingly. A few examples of such peptide-based assays for each enzymatic group, which can also be adapted to this new assay, are as follows:

Serine protease:

In the battle against West Nile Virus (WNV), inhibition of NS2B-NS3 protease has been shown to be of particular interest (Chambers, T. J. et al., *Journal of Virology* 1993, 67, 6797). In this protease, NS3 is a serine protease and its inhibition has been shown to stop the replication cycle of WNV (Chappell, K. J. et al., *Journal of Biological Chemistry* 2006, 281, 38448). A number of short peptides like KPGLKR (SEQ ID NO:14), LKKR (SEQ ID NO:15), LQYTKY (SEQ ID NO: 16), and KKRGDAK (SEQ ID NO: 17) have been reported that are susceptible to this protease and have been used as a means for designing WNV NS2B-NS3 inhibitors, using colorimetric, fluorescence, and very recently FRET-based assays (Adamek, R. N. et al., *Bioorganic & Medicinal Chemistry Letters* 2013, 23, 4848; Ezgimen, M. et al., *Antiviral Research* 2012, 94, 18; Ezgimen, M. D. et al., *Bioorganic & Medicinal Chemistry* 2009, 17, 3278; Stoermer, M. J. et al., *Journal of Medicinal Chemistry* 2008, 51, 5714). The reported peptides can easily be incorporated into the presently disclosed system for similar types of studies of inhibitors and drug discovery. Another similar example is the Dengue virus for which the same viral protease (NS3) is shown to be one of the few options for developing therapeutics (Erbel, P.; Schiering, N. et al., *Nature Structural & Molecular Biology* 2006, 13, 372; Leung, D. et al., *Journal of Biological Chemistry* 2001, 276, 45762). The same principles and similar peptide sequences can be used in the presently disclosed system for effective, low cost drug discovery.

Threonine protease:

Protein kinases and phosphatases are good potential drug targets as a result of their important regulatory effects on phosphorelation in cell growth and vitality. Protein kinases and phosphatases have been the focus of small molecule drug discovery for many years in most of the pharmaceutical companies (Blume-Jensen, P. & Hunter, T. *Nature* 2001, 411, 355). For example, a fluorescent peptide-based system is reported for development of high-throughput screening system for identifying new kinase and phosphatase drug targets (Rodems, S. M. et al., *Assay and Drug Development Technologies* 2002, 1, 9). In this system, the reported peptide is sensitive to both tyrosine and threonine proteases. A number of short peptides including EAEAIYAAPGDK (SEQ ID NO: 18), and GDQDYLSLDK (SEQ ID NO: 19) were used as protease sensitive peptides for screening of protein kinase and phosphatase. Similar peptides may be adapted for use in the presently disclosed system for drug discovery purposes.

Cysteine Protease:

Cysteine proteases are widely found in both prokaryotes and eukaryotes and are involved in many physiological processes and in a number of diseases including arthritis, tumor metastasis, and multiple sclerosis (MS). As a result, cysteine proteases have been studied as promising biomarkers for early detection of such diseases (Irani, D. N. et al., *Annals of Neurology* 2006, 59, 237; Szabelski, M. et al., *Analytical Biochemistry* 2005, 342, 20). It has been shown that cleavage of cystatin C, which is an important inhibitor of cysteine protease, in the spinal fluid of the MS patients can be used as a biomarker for early detection of the disease (Irani, D. N. et al., *Annals of Neurology* 2006, 59, 237). In another study, a large group of peptides were studied with the purpose of finding the most susceptible peptides to papain and cathepsin, two well-known cysteine proteases, by incorporating them in a fluorescence assay (Szabelski, M. et al., *Analytical Biochemistry* 2005, 342, 20). Such screening studies can be performed with the presently disclosed system as well, by developing libraries of peptides and comparing the time and intensity of aggregation among them in similar conditions.

Aspartic Proteases:

Studies of the binding preferences of malaria digestive enzyme have proven to be a pathway of discovering new peptidase-based drugs for the disease (Francis, S. E. et al., *Annual Review of Microbiology* 1997, 51, 97). During the progress of the infection, the process of hemoglobin degradation by the parasite is catalyzed by aspartic proteases, cysteine proteases, and metalloproteinases (Klemba, M. & Goldberg, D. E. *Annual Review of Biochemistry* 2002, 71, 275; Shenai, B. R. et al., *Journal of Biological Chemistry* 2000, 275, 29000). It has been suggested that aspartic peptidase may be the initiator of the digestion process of hemoglobin (Coombs, G. H. et al., *Trends in Parasitology* 2001, 17, 532). These findings suggest that peptidases are good candidates as drug targets in the battle against malaria. Finding the right peptidase and designing the corresponding anti-malaria therapeutics requires screening many substrates to identify peptide specificity. One such effort is reported by Beyer et al. through changing single amino acid sequence in each peptide. Through this process they were able to build a library of peptides with a range of susceptibility to aspartic protease (Beyer, B. B. et al., *Biochemistry* 2005, 44, 1768). The presently disclosed system can be easily modified to accommodate different peptides for similar tasks, and to develop a library of peptides for specific protease (e.g., the quantification aspect would be equivalent and the kinetics of the enzymatic reaction is essentially the absorbance vs. time curve).

Metalloproteinase:

As described elsewhere herein, this family of proteases is of great importance as biomarkers and in diagnosis. Examples of how the system can be designed and used for protease detection and quantification are presented in the Examples below.

Use of Non-Protease Peptide Modifications to Induce Changes in Environmentally-Responsive Polymers and Biopolymers.

The modular design of the presently disclosed system and the flexible nature of its design provide the opportunity to use non-protease modifications to affect the characteristics of the polymer or biopolymer such that they induce a measurable change in the solution (e.g., precipitation and fluorescence). This can include splicing the peptide to induce aggregation or FRET signaling by using inteins (Paulus, H. *Annual Review of Biochemistry* 2000, 69, 447), kinase reactions (Martin, K. et al., *Proteomics* 2003, 3, 1244), phosphorylation, glycosylation, hydroxylation, and ligation. In general any peptide modification that can lead to a change of responsiveness of environmentally-responsive polymers and biopolymers in the presently disclosed assay has the potential to be used as a triggering method. Hence the presently disclosed system can not only be used for detection and quantification of protease but also it can be used to monitor other post-translational modifications in peptides and proteins.

Use of Other Environmentally-Responsive Polymers and Biopolymers.

The change in optical density of the solution is induced through the aggregation of the hydrophobic segment of the molecules as a result of the digestion of the hydrophilic residues, as described in the Examples below. The only requirement for these molecules is that they should be hydrophobic enough at the assay temperature that detaching the hydrophilic head group leads to the aggregation of the tails. The hydrophobicity of these chains can be inherent or can be induced by changing the environmental conditions for certain polymers and biopolymers. The exemplary systems described in Examples 1 and 2 are designed based on using elastin-like polypeptides. However, any temperature responsive polymer or any peptide domain with high enough hydrophobicity can potentially be used instead, and the system will function the same way as long as the phase transition temperature can be controlled below about 40'C. A recent review of temperature responsive homopolymers and copolymers listed more than 30 different temperature-responsive macromolecules (Fitzpatrick, L. E. et al., *Expert Review of Medical Devices* 2012, 9, 339). However, typical polymers with lower critical solution temperature (LCST) behavior are based on N-isopropylacrylamide (NIPAM) (Schild, H. G. *Progress in Polymer Science* 1992, 17, 163), N,N-diethylacrylamide (DEAM) (Idziak, I. et al., *Macromolecules* 1999, 32, 1260), methylvinylether (MVE) (Mikheeva, L. M. et al., *Macromolecules* 1997, 30, 2693), and N-vinylcaprolactam (NVCl) (Van Durme, K. et al., *Macromolecules* 2004, 37, 1054). In addition to LCST polymers, it is possible to use solutions with upper critical solution temperature (UCST), for example a combination of acrylamid and acrylic acid (Aoki, T. et al., *Macromolecules* 1994, 27, 947). These chemically-synthesized or peptide-based polymers can be conjugated to enzyme-sensitive peptides and aggregate into large particles, upon digestion of the head group.

Use of Insoluble Protease-Sensitive Peptides.

The system described in Example 1 below uses a charged, hydrophilic, enzyme-sensitive peptide as the micelle-forming head group to keep the hydrophobic tail from bulk aggregation, above the transition temperature of the temperature-responsive polymer. However, insoluble protease-sensitive peptides can also be used in the presently disclosed system by implementing changes in the design of the molecules. For example, by placing the protease-sensitive peptide between a hydrophobic polymer or biopolymer and a long, hydrophilic polymer or polypeptide, the digestion of the peptide at temperatures above the transition temperature of the responsive polymer will result in drastic change in optical density. An example of such system is presented herein below.

Use of Non-Micelle-Forming Constructs.

Although several examples presented herein below focus on using micelle-forming constructs, it is also possible to design the system such that the polypeptide molecules transition directly from soluble to insoluble when the molecules are digested by the enzymes. For elastin-like polypeptides (ELPs), the charged enzyme-sensitive peptide fused to the ELP molecule increases the transition temperature of the ELP molecule (Christensen, T. et al., *Biomacromolecules* 2013, 14, 1514). This change in transition temperature can be exploited as a means to detect and quantify the protease in the solution, similar to the way described for micelle-forming constructs. However, it is also possible to use non-responsive hydrophobic polymers which are solubilized by attaching to a hydrophilic polymer. The cleavage of the protease-sensitive peptide which is placed in between the two segments will cause a similar bulk aggregation in the solution.

The very simple nature of the presently disclosed assays is a great advantage over most commercially available protease assays. The assays are also very flexible, and can be adapted to many different proteases as described above. This is great advantage from a manufacturing point of view as it reduces the lead time for new products. In addition, only a few instruments are necessary to run these assays; the assays can be run in any lab or facilities with the capability of measuring optical density of a solution either in single holders or plate readers. The assays can be run using essentially any wave length. The simplicity of these assays is of great importance, especially if the assays need to be run as a point of care diagnosis system in underdeveloped countries or communities. The low cost of the assay is also very important for both commercialization and for making the assays accessible to populations in developing countries.

Accordingly, in one embodiment, the presently disclosed subject matter provides a method for detecting protease activity in a sample comprising the steps of: a) contacting the sample with amphiphilic fusion polypeptides, wherein each of the fusion polypeptides comprise a hydrophobic domain and a hydrophilic domain separated by a protease substrate domain, wherein the fusion polypeptides self-assemble into micelles, and further wherein the micelles comprise coronae comprising the protease substrate domains; b) providing conditions in which protease present in the sample will cleave the protease substrate domains, whereby the hydrophobic domains of the micelles aggregate into particles at a detectable aggregation rate; and c) detecting the aggregation rate of particles in the sample; wherein the aggregation rate of particles in the sample is positively correlated to the protease activity in the sample. The protease substrate domains may comprise a cleavage site for a protease selected from the group consisting of a serine protease, a threonine protease, a cysteine protease, an aspartic protease, a glutamic protease, and a metalloproteinase. In particular embodiments, the aggregation rate of particles may be detected by optical turbidimetry or visual observation.

In another embodiment, the presently disclosed subject matter provides a method for detecting protease activity in a sample comprising the steps of: a) contacting the sample with amphiphilic fusion polypeptides, wherein each of the fusion polypeptides comprise a hydrophobic phase transition domain and a hydrophilic domain separated by a protease substrate domain, wherein the fusion polypeptides self-assemble into micelles in response to a stimulus that triggers phase transition of the phase transition domains, and further wherein the micelles comprise coronae comprising the protease substrate domains; b) presenting the stimulus to the fusion polypeptides, whereby the fusion polypeptides self-assemble into micelles; c) providing conditions in which protease present in the sample will cleave the protease substrate domains, whereby the hydrophobic phase transition domains of the micelles aggregate into particles at a detectable aggregation rate; and d) detecting the aggregation rate of particles in the sample; wherein the aggregation rate of particles in the sample is positively correlated to the protease activity in the sample. In a particular embodiment, the stimulus is temperature. In another embodiment, the hydrophobic phase transition domains display lower critical solution temperature (LCST) behavior. In a particular embodiment, the hydrophobic phase transition domains aggregate into particles at a temperature greater than or equal to a temperature $T_t$, wherein the fusion polypeptide has a critical micellization temperature (CMT), and wherein the method is performed at a temperature greater than both the CMT and $T_t$.

In yet other embodiments, the hydrophobic phase transition domains comprise elastin-like polypeptides, for example the hydrophobic phase transition domains may comprise the amino acid sequence (GVGVP)60 (SEQ ID NO:23). In other embodiments, the hydrophilic domains comprise an anionic peptide, for example the hydrophilic domains may comprise the amino acid sequence DEGQQD-DEEGY (SEQ ID NO:11) or a long hydrophilic peptide sequence comprising the amino acid sequence (VPGAGVPGGG)30 (SEQ ID NO:5). In further embodiments, the protease substrate domains comprise a cleavage site for a protease selected from the group consisting of a serine protease, a threonine protease, a cysteine protease, an aspartic protease, a glutamic protease, and a metalloproteinase, particularly wherein the protease is Matrix metalloproteinase-1 (MMP-1) and the protease substrate domains comprise an amino acid sequence selected from the group consisting of DGQVPMSMRGG (SEQ ID NO:10) and VPMSMRGG (SEQ ID NO:12). In particular embodiments, the fusion polypeptides are selected from the group consisting of the amino acid sequence M(GVGVP)60GDGQVPMSMRGGDDEGQQDDEEGY (SEQ ID NO:1) and the amino acid sequence MSKGPGWGVG(VPGVG)60GDGQVPMSMRGGDDEGQQDDEE(VPGAGVPGGG)30YG (SEQ ID NO:2). Alternatively, where the protease is Prostate Specific Antigen (PSA), the protease substrate domains may comprise the amino acid sequence SSIYSQTEEQQ (SEQ ID NO:13) and the fusion polypeptides may comprise the amino acid sequence M(GVGVP)60GDGQSSIYSQTEEQQDDEEG (SEQ ID NO:6). In particular embodiments, the aggregation rate of particles may be detected by optical turbidimetry or visual observation.

In another embodiment, a method for detecting protease activity in a sample is provided comprising the steps of: a) contacting the sample with fusion polypeptides, wherein each of the fusion polypeptides comprise a phase transition domain, a protease substrate domain and an optional hydrophilic or a hydrophobic domain, wherein the phase transition domains display upper critical solution temperature (UCST) behavior; b) providing conditions in which protease present in the sample will cleave the protease substrate domains, whereby the phase transition domains aggregate into particles at a detectable aggregation rate; and c) detecting the aggregation rate of particles in the sample; wherein the aggregation rate of particles in the sample is positively correlated to the protease concentration in the sample. In further embodiments, the hydrophilic domains comprise anionic peptides, for example wherein the hydrophilic domains comprise the amino acid sequence DEGQQDDEEGY (SEQ ID NO: 11). The protease substrate domains may comprise a cleavage site for a protease selected from the group consisting of a serine protease, a threonine protease, a cysteine protease, an aspartic protease, a glutamic protease, and a metalloproteinase, particularly wherein the protease is Matrix metalloproteinase-1 (MMP-1) and the protease substrate domains comprise the amino acid sequence DGQVPMSMRGG (SEQ ID NO: 10). In particular embodiments, the fusion polypeptides are selected from the group consisting of the amino acid sequence M(YPSDGRGQ)$_{40}$YGDGQVPMSMRGGDEGQQDDE-EGY (SEQ ID NO:7), the amino acid sequence M(YPSDGRGQ)$_{20}$YGDGQVPMSMRGGDEGQQDDE-EGY (SEQ ID NO: 20), the amino acid sequence M(YGRGDSA)$_{16}$YGDGQVPMSMRGGDEGQQDDE-EGY (SEQ ID NO:21), and the amino acid sequence M(YGRGDSA)$_{24}$YGDGQVPMSMRGGDEGQQDDE-EGY (SEQ ID NO:22). In particular embodiments, the aggregation rate of particles may be detected by optical turbidimetry or visual observation.

In another embodiment, a method for detecting enzyme activity in a sample is provided comprising the steps of: a) contacting the sample with fusion polypeptides, wherein each of the fusion polypeptides comprise a phase transition domain and an enzyme substrate domain; b) providing conditions in which enzyme present in the sample will bind to and modify the enzyme substrate domains, whereby a transition temperature for the fusion polypeptides is increased above the temperature of the sample, and further wherein the fusion polypeptides aggregate into particles at a detectable aggregation rate; and c) detecting the aggregation rate of particles in the sample; wherein the aggregation rate of particles in the sample is positively correlated to the enzyme activity in the sample. In one embodiment, the enzyme is a Protein arginine deiminase (PAD), particularly Protein arginine deiminase 4 (PAD4). In a particular embodiment, the fusion polypeptide comprises the amino acid sequence $(GSGRGKGGKGLG(VPGVG)_x)_y$ (SEQ ID NO:8). In another particular embodiment, the aggregation rate of particles may be detected by optical turbidimetry or visual observation.

The term "polypeptide" refers to a polymer of amino acids without regard to the length of the polymer; thus, peptides, oligopeptides, and proteins are included within the definition of polypeptide. This term also does not specify or exclude post-translation modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The terms "fusion" and "chimeric" or "chimera" are used interchangeably herein and refer to a polypeptide or protein created by joining two or more polypeptide sequences which are not naturally joined together, or a polynucleotide or gene created by joining two or more polynucleotide sequences which are not naturally joined together. For example, a fusion polypeptide may be expressed from a single fusion polynucleotide encoding the fusion polypeptide.

The term "purified polypeptide" is used herein to describe a polypeptide of the presently disclosed subject matter that has been separated from other compounds including, but not limited to nucleic acids, lipids, carbohydrates and other proteins. A polypeptide is substantially pure when a sample contains at least about 50%, preferably 60 to 75%, of a single polypeptide sequence. A substantially pure polypeptide typically comprises about 50%, preferably 60 to 90%, more preferably 95 to 99% weight/weight of a protein sample. Polypeptide purity or homogeneity is indicated by a number of means well known in the art, such as agarose or polyacrylamide gel electrophoresis of a sample, followed by visualizing polypeptide bands upon staining the gel. For certain purposes, higher resolution can be provided by using HPLC or other means well known in the art.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotides could be part of a vector and/or such polynucleotide or polypeptide could be part of a composition, and still be isolated in that the vector or composition is not part of its natural environment.

The term "purified" does not require absolute purity; rather, it is intended as a relative definition. Purification of starting material or natural material to at least one order of magnitude, preferably two or three orders, and more preferably four or five orders of magnitude is expressly contemplated. As an example, purification from 0.1% concentration to 10% concentration is two orders of magnitude.

The term "purified polypeptide" is used herein to describe a polypeptide of the presently disclosed subject matter that has been separated from other compounds including, but not limited to nucleic acids, lipids, carbohydrates and other proteins. A polypeptide is substantially pure when a sample contains at least about 50%, preferably 60 to 75%, of a single polypeptide sequence. A substantially pure polypeptide typically comprises about 50%, preferably 60 to 90%, more preferably 95 to 99% weight/weight of a protein sample. Polypeptide purity or homogeneity is indicated by a number of means well known in the art, such as agarose or polyacrylamide gel electrophoresis of a sample, followed by visualizing polypeptide bands upon staining the gel. For certain purposes higher resolution can be provided by using HPLC or other means well known in the art.

As described herein, isolated, purified, and recombinant polypeptides may comprise a contiguous span of at least 6 amino acids, preferably at least 8 to 10 amino acids, more preferably at least 12, 15, 20, 25, 30, 40, 50, or 100 amino acids of a reference sequence. In other preferred embodiments the contiguous stretch of amino acids comprises the site of a mutation or functional mutation, including a deletion, addition, swap or truncation of the amino acids in a polypeptide sequence.

Polypeptides may be isolated from human or mammalian tissue samples or expressed from human or mammalian genes. Polypeptides may be made using routine expression methods known in the art. The polynucleotide encoding a desired polypeptide may be ligated into an expression vector suitable for any convenient host. Both eukaryotic and prokaryotic host systems are used in forming recombinant polypeptides, and a summary of some of the more common systems is provided herein. The polypeptide may then be isolated from lysed cells or from the culture medium and purified to the extent needed for its intended use. Purification may be by any technique known in the art, for example, differential extraction, salt fractionation, chromatography, centrifugation, and the like (See, for example, Abbondanzo et al. (1993) Methods in Enzymology, Academic Press, New York. pp. 803-823).

In addition, shorter protein fragments may be produced by chemical synthesis. Alternatively proteins of the presently disclosed subject matter are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis, for example.

Reference cDNA may be used to express polypeptides. The nucleic acid encoding the polypeptide to be expressed is operably linked to a promoter in an expression vector using conventional cloning technology. For example, a membrane bound polypeptide in the expression vector may comprise the full coding sequence for the polypeptide or a portion thereof. For example, the insert may encode a polypeptide comprising at least 10 consecutive amino acids of a membrane bound polypeptide.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters, including default parameters for pairwise alignments.

Variants of polypeptides according to the presently disclosed subject matter include, without being limited to, amino acid sequences which are at least 70% identical, e.g., at least 75%, 80%/a, 85%, 90%, 91%, 92%, 93%, 94%, 95%, 96%, 97%, 98%, or 99% identical to a reference polypeptide, and preferably at least 99.5% identical, and more preferably at least 99.8% identical to a reference polypeptide.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al. (1990) *J. Mol. Biol.* 215:403-410, and DNASTAR (DNASTAR, Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Methods of Detecting and Monitoring Diseases

The presently disclosed assays may be used within methods for the early detection of a number of infectious, inflammatory, and cardiovascular diseases, as well as cancers. It has been shown that in certain diseases, an increase in the concentration of certain proteases (e.g. MMP) is an indication of the disease even before the existence of clinical symptoms (Sato, H. et al., Nature 1994, 370, 61). Simple and low cost assays provide the opportunity to monitor high risk individuals for the first indication of possible abnormalities. Further tests can then be done for patients with abnormal test results. Simple and low cost assays can also potentially prevent unnecessary invasive or expensive tests.

The presently disclosed assays may also be used to monitor the progression or recurrence of diseases (e.g., cancer) or the efficacy of a therapeutic treatment by monitoring changes in enzyme or protease levels. The low cost of the assays can be a great advantage when it is necessary to monitor patients for long periods of time. By contrast, currently available protease tests are expensive and laborious.

Accordingly, in one embodiment, a method of predicting or diagnosing a disease in a subject is provided comprising: a) obtaining a biological sample from the subject; b) detecting the activity of an enzyme in the biological sample using any of the methods for detecting enzyme activity described herein; and c) comparing the activity of the enzyme in the biological sample to the activity of the enzyme from a control sample from the subject or a control sample from subjects who do not have the disease; wherein a significant difference between the activity of the enzyme in the biological sample and the control sample is indicative that the subject has or is susceptible to developing the disease. In particular embodiments, the disease is selected from the group consisting of an infectious disease, an inflammatory disease, a cardiovascular disease, and a cancer. In further embodiments, the enzyme is a protease, particularly wherein the protease is selected from the group consisting of a serine protease, a threonine protease, a cysteine protease, an asparatic protease, a glutamic protease, and a metalloproteinase.

In another embodiment, a method of monitoring the progression or recurrence of a disease in a subject is provided comprising: a) obtaining a biological sample from the subject; b) detecting the activity of an enzyme in the biological sample using any of the methods for detecting enzyme activity described herein; and c) comparing the activity of the enzyme in the biological sample to the activity of the enzyme from a control sample from the subject or a control sample from subjects who do not have the disease; wherein a significant difference between the activity of the enzyme in the biological sample and the control sample is indicative of the progression or recurrence of the disease in the subject. In particular embodiments, the disease is selected from the group consisting of an infectious disease, an inflammatory disease, a cardiovascular disease, and a cancer. In further embodiments, the enzyme is a protease, particularly wherein the protease is selected from the group consisting of a serine protease, a threonine protease, a cysteine protease, an asparatic protease, a glutamic protease, and a metalloproteinase.

In another embodiment, a method for determining the efficacy of a therapeutic treatment for a disease in a subject undergoing the treatment is provided comprising: a) obtaining a biological sample from the subject; b) detecting the activity of an enzyme in the biological sample using any of the methods for detecting enzyme activity described herein; and c) comparing the activity of the enzyme in the biological sample to the activity of the enzyme from a control sample from the subject or a control sample from subjects who do not have the disease; wherein a significant difference between the activity of the enzyme in the biological sample and the control sample is indicative of the efficacy of the therapeutic treatment of the disease in the subject. In particular embodiments, the disease is selected from the group consisting of an infectious disease, an inflammatory disease, a cardiovascular disease, and a cancer. In further embodiments, the enzyme is a protease, particularly wherein the protease is selected from the group consisting of a serine protease, a threonine protease, a cysteine protease, an asparatic protease, a glutamic protease, and a metalloproteinase.

As used herein, the term "comparing" refers to making an assessment of how the proportion, level, concentration, or activity of an enzyme such as a protease in a sample relates to the proportion, level, concentration, or activity of an enzyme such as a protease in a control sample. For example, "comparing" may refer to assessing whether the proportion, level, concentration, or activity of an enzyme such as a protease in a sample is the same as, more or less than, or different in proportion, level, concentration, or activity the corresponding enzyme such as a protease in a standard or control sample.

As used herein, the terms "measuring" and "determining" refer to methods which include detecting the proportion, level, concentration, or activity of an enzyme such as a protease in a sample.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. It will be appreciated that, although not precluded, treating a disease, disorder or condition does not require that the disease, disorder, condition or symptoms associated therewith be completely eliminated.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition.

As used herein, the term "subject at risk" of getting a disease refers to estimating that a subject will have a disease or disorder in the future based on the subject's current symptoms, family history, lifestyle choices, and the like.

As used herein, the term "indicative" or "likely" means that the event referred to is probable. For example, if the methods of the presently disclosed subject matter result in a conclusion that the subject is likely to develop a type of cancer, it is probable that the subject will develop a type of cancer.

As used herein, the term "diagnosing" refers to the process of attempting to determine or identify a disease or disorder.

The subject diagnosed, monitored, and/or treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for treating an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

As used herein, the term "sample" refers to any material suspected of containing an enzyme or protease. The term "biological sample" comprises a bodily fluid obtained from a living organism. A biological sample is preferably an aqueous mixture, for example, urine, whole blood, plasma, serum, saliva, semen, stool, sputum, cerebral spinal fluid, tears, mucus or the like, but preferably is plasma or serum, and more preferably is human plasma or human serum.

As used herein, the term "control sample", "corresponding control", or "appropriate control" means any control or standard familiar to one of ordinary skill in the art useful for comparison purposes.

Drug Discovery

The presently disclosed assays are also useful in the area of drug discovery. For example, protease inhibitors may be identified via high throughput screening of libraries of potential peptides. Such compounds can then be used directly or indirectly in the treatment of related diseases. Furthermore, since the presently disclosed assays are not only limited to protease monitoring, they may be used to study other post-translational modifications in certain proteins in the process of drug development.

Accordingly, in one embodiment, a method of identifying an agent that inhibits the activity of an enzyme is provided comprising: a) detecting the activity of an enzyme in a sample using any of the methods for detecting enzyme activity described herein; b) contacting the sample with a candidate agent; and c) comparing the activity of the enzyme in the sample after contact with the candidate agent to the activity of the enzyme in the sample before contact with the candidate agent; wherein a significant decrease in the activity of the enzyme in the sample after contact with the candidate agent compared to the activity of the enzyme in the sample before contact with the candidate agent is indicative that the candidate agent is an agent that inhibits the activity of the enzyme. In a particular embodiment, the enzyme is a protease, more particularly a protease is selected from the group consisting of a serine protease, a threonine protease, a cysteine protease, an asparatic protease, a glutamic protease, and a metalloproteinase.

Detection Devices and Systems

Figure 22A:
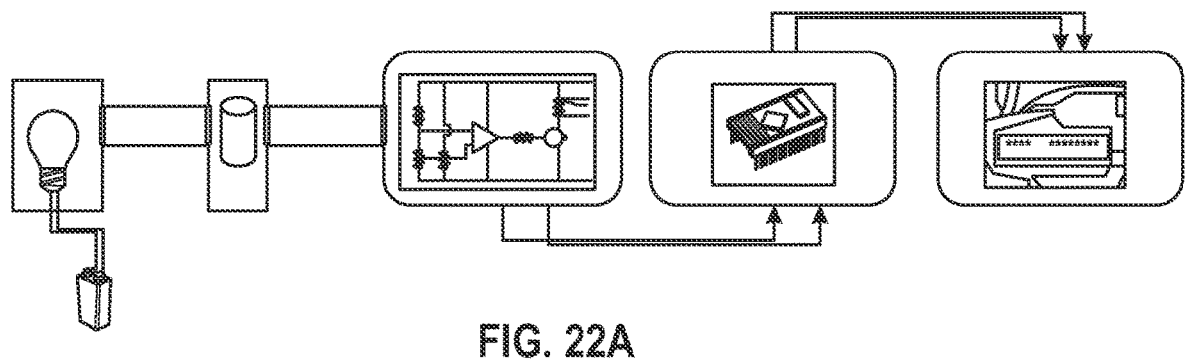
FIG. 22 shows: (A) a flowchart illustration of a design for a portable low cost detection device based on the presently disclosed modular assay system; and (B) a photograph of a portable low cost detection device according to the design illustrated in (A) for performing the presently disclosed modular assay system.

The presently disclosed subject matter also relates to a device and/or system for carrying out any of the assays disclosed herein, particularly portable, low cost detection devices and/or systems as point of care technology. A flowchart illustration for one possible embodiment of the device is shown in FIG. 22A. For example, in one embodiment, light from an LED lamp powered by a battery is shined on a sample. A photo-detector detects the light and converts the light into electrical output signal. The intensity of light which passes through the sample is proportional to the turbidity of the sample, and therefore, based on the intensity of the incoming light, the output signal changes. The output signal from the photo-detector is sent to a small micro-controller that is programmed such that when the signal is above a certain threshold it starts a timer, and when it falls below a preset value it stops the timer. The resulting time is the "aggregation time" and is the output of the assay device.

Accordingly, any of the assays disclosed herein may be embodied as a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While certain embodiments have been described, these embodiments have been presented by way of example only, and are not intended to limit the scope of the inventions. Indeed, the novel methods, devices, and systems described herein may be embodied in a variety of other forms. Furthermore, various omissions, substitutions, and changes in the form of the methods, devices, and systems described herein may be made without departing from the spirit of the inventions. The accompanying claims and their equivalents are intended to cover such forms or modifications as would fall within the scope and spirit of the inventions.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Unregulated changes in protease activity are linked to many diseases including cancer. Fast, accurate, and low cost assays for detection of these changes would be useful for early diagnosis and monitoring of these diseases and could also be used as platforms for the discovery of new drugs. The present example describes a new methodology for the simple detection and quantification of protease activity in buffer and human serum. The assay is based on recombinant diblock polypeptides that undergo temperature- or salt-triggered micellization in water. The coronae of the micelles are linked to the water insoluble cores by a peptide substrate that is cleaved in the presence of the target protease. Protease cleavage of the diblock polypeptide triggers the aggregation of the core-forming segment, leading to a change in solution optical density, which can be used to detect the presence of, and to quantify the concentration of, protease. Matrix metalloproteinase-1 (MMP-1) was used as a model protease and it was found that peptide aggregation time was proportional to enzyme concentration over a range from endogenous MMP-1 level in human serum (~3 ng/mL) to 100 ng/mL (0.15 nM to 5 nM) in 40% human serum and 1 ng/mL to 100 ng/mL in buffer. The assay does not require any intermediate steps or sophisticated data analysis and the modular design of the assay system is amenable to straightforward adaptation for the detection of a wide range of proteases.

EXPERIMENTAL

Materials

Human MMP-1 catalytic domain (recombinant, produced in E. coli, 19.9 kDa, >95% purity) and MMP inhibitor (N-isobutyl-N-(4-methoxyphenylsulfonyl)glycyl hydroxamic acid) were purchased from Enzo Life Sciences (Farmingdale, N.Y.). The pET24+ cloning vector was purchased from Novagen (Madison, Wis.). Restriction enzyme, quick ligation kit, and phosphatase were purchased from New England Biolabs (Ipswich, Mass.). BL21 E. coli cells were purchased from Bioline (Taunton, Mass.). All the salts were purchased from Alfa Aesar (Ward Hill, Mass.). All the Ecoli cultures were grown in TB media purchased from MO BIO laboratories Inc. (Carlsbad, Calif.). The DNA extraction kit, DNA gel purification kit, and PCR purification kits were purchased from Qiagen Inc. (Germantown, Md.). Sterilized human serum samples were from healthy male serum purchased from GemCells (Sacramento, Calif.).

Gene Design and Construction.

The ELP gene corresponding to 60 repeats of (VPGVG) (SEQ ID NO:4) was previously constructed using recursive directional ligation by plasmid reconstruction (Pre-RDL) as described elsewhere (McDaniel, J. R. et al., *Biomacromolecules* 2010, 11, 944-952). We chose the MMP-substrate peptide, VPMSMRGG (SEQ ID NO: 12), based on previous studies showing its high susceptibility to cleavage by MMP-1 (Patterson, J. & Hubbell, J. A. *Biomaterials* 2010, 31, 7836-7845; Turk, B. E. et al., *Nature Biotechnology* 2001, 19, 661-667). The peptide is water soluble and is cleaved by MMP-1 between serine and methionine. To ensure that the ELP aggregates into micelles and that the MMP-1 substrate peptide was accessible to the enzyme, we added a series of nucleotides encoding hydrophilic charged amino acids to the C-terminal end encoding for the MMP-sensitive peptide and then fused these to the gene for the ELP using Pre-RDL. The final sequence combining the genes for the ELP, the MMP-1 sensitive sequence and the additional hydrophilic residues (which we refer to herein as ELP-substrate fusion) was confirmed by DNA sequencing (Eton Biosciences) and is M(GVGVP)$_{60}$GDGQVPMSMRGGDDEGQQDDEEGY (SEQ ID NO:1).

Polypeptide Expression and Purification.

We transformed the ELP-substrate fusion gene into chemically competent E. coli BL21 cells and incubated it overnight at 37° C. on agar plates supplemented with kanamycin. One colony was used to inoculate a total volume of 60 mL of sterilized Terrific Broth (TB) media supplemented with 45 µg/mL of kanamycin as a starter culture. The culture was shaken overnight at 220 rpm and 37° C. and then was used to inoculate sterilized TB media in 4-L flasks each containing 1 L of media, supplemented with 45 µg/mL of kanamycin. We then let the media shake at 37° C. and 220 rpm for approximately 6 h before inducing it with 0.1 mM isopropyl β-D-1-thiogalactopyranoside (IPTG). The bacterial culture was harvested after 12 to 14 h and centrifuged at 4° C. and 4,500 rpm for 15 min. The harvested cells were lysed by sonication at 85 W, in cycles of 10 s on and 30 s off for total sonication time of 3 min.

We purified the peptides from the cells using inverse transition cycling (ITC), which is described in detail elsewhere (Meyer, D. E. & Chilkoti, A. *Nature Biotechnology* 1999, 17, 1112-1115). In this method, the reversible transition of ELPs from water-soluble to insoluble at specific temperatures is exploited to purify the polypeptide by a series of hot and cold centrifugation cycles.

Polypeptide Characterization.

We confirmed the purity and molecular weight of the purified peptides by electrophoresis (10-20% gradient Tris-glycerol SDS-PAGE, Thermo Scientific, CA) and by matrix-assisted laser desorption/ionization mass spectrometry. Mass spectrometry samples were prepared by mixing the enzymatic reaction product with sinapinic acid in 1:10 ratio. 1 µL of the sample/matrix mixture was then loaded on the grid and the measurements were performed on a Voyager-DE-Pro instrument (Applied Biosystems, Germany). To determine the concentration of the ELP-substrate fusion solutions we used a calculated extinction coefficient (Gill, S. C. & Vonhippel, P. H. *Analytical Biochemistry* 1989, 182, 319-326) or lyophilized the polypeptide solution. We studied the thermal behavior of the ELP-substrate fusion constructs in both proteolysis buffer (see below) and diluted human serum in the presence and absence of MMP-1 using optical turbidimetry on a temperature-programmed UV-vis spectrometer (Cary 300, Agilent Technologies). To characterize the size of the micelles and aggregates, we used single angle dynamic light scattering (DLS; DynaPro, Protein Solution).

Measurement of Protease Activity.

We performed the proteolysis reactions either in 100% protease buffer or in a mixture of human serum and buffer (40% (v/v) serum, 50% (v/v) buffer, 10% (v/v) ELP-substrate solution in water). The proteolysis buffer (100 mM HEPES, CaCl$_2$ 20 mM, MgCl$_2$ 1.0 mM, ZnCl$_2$ 100 µM, NaCl 0.5 M for diluted serum and 0.1 M for buffer solutions) was made experimentally in our lab based on previously published assays (Patterson, J. & Hubbell, J. A. *Biomaterials* 2010, 31, 7836-7845; Turk, B. E. et al., *Nature Biotechnology* 2001, 19, 661-667; Lowe, S. B. et al., *Acs Nano* 2012, 6, 851-857). We investigated proteolysis in two ways. In the first approach, we incubated solutions of the ELP-substrate fusion with MMP-1 (100 ng/mL) for 12 h at 40° C. temperature and measured the optical density at 350 nm (OD$_{350}$) before and after the incubation. In the second approach, we incubated the ELP-substrate fusion with varying concentrations of MMP-1 (0.02 ng/mL to 200 ng/mL) in buffer or in diluted human serum, at 40° C. or 37° C. respectively, a temperature that is above the CMT of the ELP, and monitored the changes OD$_{350}$ as a function of time (kinetic study). For the kinetic studies, we added the enzyme to the solution after the optical density of the solution reached a steady-state value and repeated the experiments at least three times.

Results and Discussion

Design of the Assay.

We chose matrix metalloprotease-1 (MMP-1) as the model protease analyte because of its role in several diseases including cancer (Sato, H. et al., *Nature* 1994, 370, 61-65), cardiovascular (Schwartzkopff, B. et al., *European Journal of Heart Failure* 2002, 4, 439-444), and infectious diseases (Elkington, P. T. G. et al., *Clinical and Experimental Immunology* 2005, 142, 12-20). Moreover, among the MMP family, MMP-1 has one of the lowest endogenous concentrations in the healthy human serum, which makes its detection and quantification a significant challenge (Karapanagiotidis, G. T. et al., *Journal of Cardiothoracic Surgery* 2009, 4, 59). Our assay for MMP-1 uses a recombinant polypeptide that has three segments: a stimuli responsive elastin-like polypeptide (ELP), a protease substrate sequence and a highly charged terminal sequence (FIG. 1A).

The first segment is a thermally responsive ELP, which was chosen because it has several important properties relevant to the design of the assay. It exhibits lower critical solution temperature (LCST) phase transition behavior; below its transition temperature ($T_t$) an ELP is water soluble, while above its $T_t$, the ELP molecules aggregate into micron-sized particles (L. H. Sperling *Introduction to Physical Polymer Science*; Forth Edition ed.; Wiley-Interscience, 2006). The second reason we chose to use an ELP is that ELPs can be designed to exhibit temperature triggered self-assembly into micelles (Dreher, M. R. et al., *Journal of the American Chemical Society* 2008, 130, 687-694; McDaniel, J. R. et al., *Angewandte Chemie-International Edition* 2013, 52, 1683-1687; Simnick, A. J. et al., *Acs Nano* 2010, 4, 2217-2227) whose coronae we use to display copies of a protease substrate (FIG. 1B). Third, ELPs and their fusion peptides can be recombinantly expressed at high yield and are readily purified through inverse transition cycling (Chow, D. C. et al., *Biotechnology Progress* 2006, 22, 638-646). We chose (GVGVP)$_{60}$ as the model ELP because it has a soluble unimer-aggregate $T_t$ of ≈37° C. at a concentration of 100 µM, which we chose as the substrate concentration for the assay.

The second component of the modular polypeptide is a protease substrate that is fused to the ELP. We chose the DGQVPMSMRGG (SEQ ID NO: 10) sequence because it is a substrate for MMP-1. The third module is DEGQQDDE-EGY (SEQ ID NO: 11), an anionic peptide that was appended to the hydrophilic protease substrate to provide amphiphilicity to drive the entire ELP-substrate fusion peptide to self-assemble into micelles at the physiological temperature of the assay. Addition of MMP-1 to the solution containing these micelles results in cleavage of the micellar peptide sequences, which abrogates their amphiphilicity, and hence self-assembly of the micelles. Disruption of self-assembly by proteolysis liberates free ELP from the micelles' cores, which spontaneously aggregate into large particles as the $T_t$ of the ELP is below the operating temperature of the assay (FIG. 1C). This design hinges on the selection of an ELP sequence that has a unimer to aggregate $T_t$ that is lower or the same as the critical micellization temperature (CMT) of the ELP-substrate fusion peptide, which in turn is lower than the temperature at which the assay is carried out. The analytical basis of this assay is the formation of large aggregates that can be detected either visually or by measuring the changes in optical density of the solution. As the cleavage rate of the peptide is proportional to the concentration of enzyme in the solution, we hypothesized that the aggregation time will depend on enzyme concentration, so that the aggregation time would provide a read-out of the enzyme concentration.

Lysis of the ELP-Substrate Fusion by MMP-1.

Figure 2:
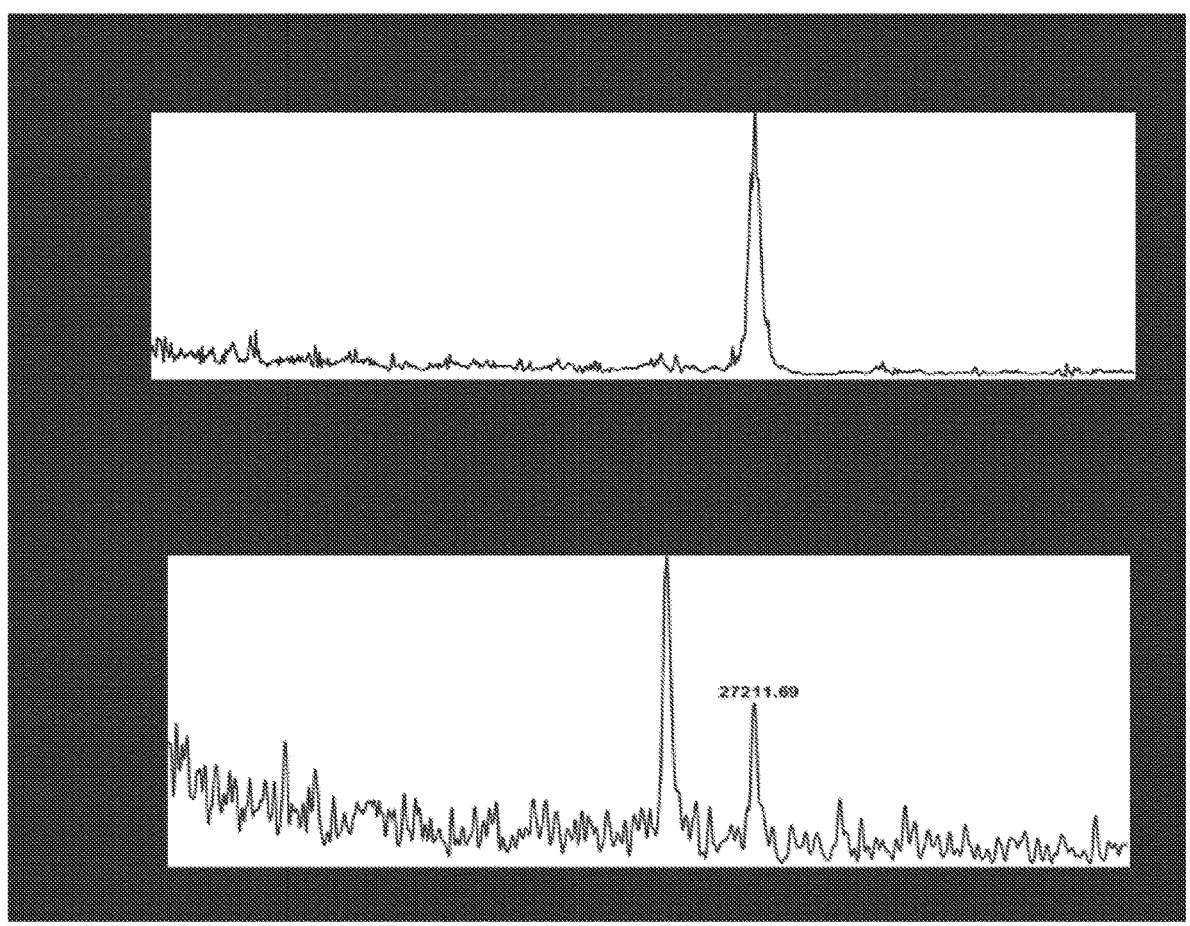
FIG. 2 shows mass spectrometry of ELP-substrate fusion (100 µM) in protease buffer (A) prior to enzymatic cleavage and (B) after incubation for 2 hours with 100 ng/mL of enzyme.
Figure 3:
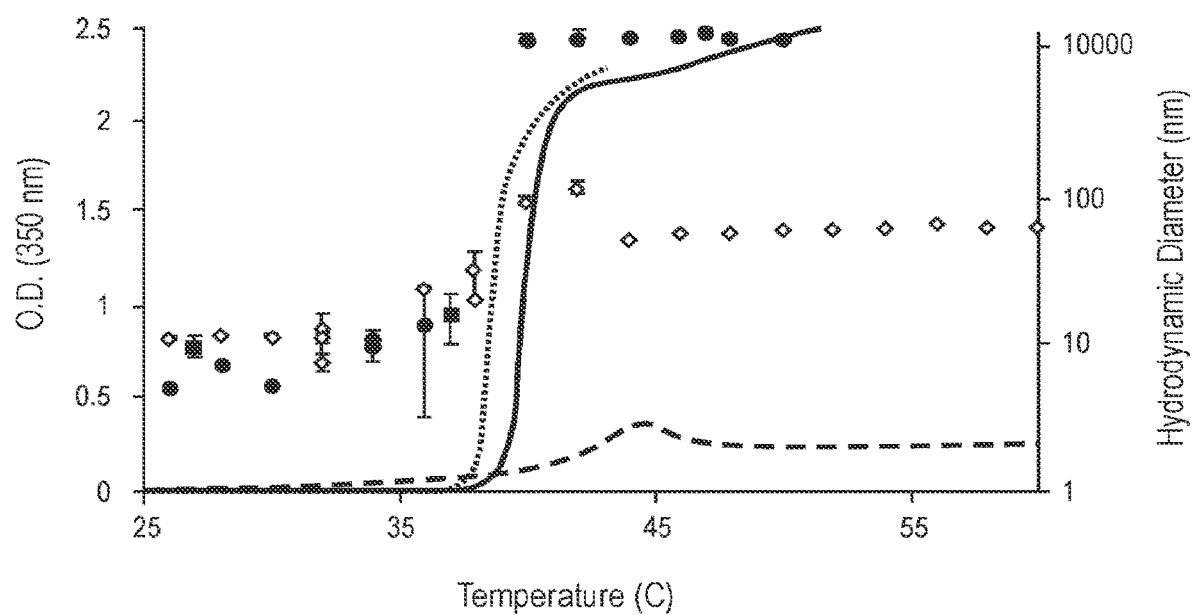
FIG. 3 shows optical density (O.D.) at 350 nm (lines) and hydrodynamic diameters from DLS (points) of ELP-substrate fusion (100 µM) in buffer as a function of temperature for (i) peptides prior to enzymatic reaction (dashed line, diamonds) and (ii) peptides incubated with 100 ng/mL of enzyme for 12 hours (solid line, dots). The dotted line and solid squares indicate optical density and hydrodynamic diameters of the $(VPGVG)_{60}$ (SEQ ID NO:4) control (100 µM) in buffer.

We used mass spectrometry to examine the cleavage of the MMP-1 substrate peptide in the ELP-substrate fusion by measuring the molecular weight of the polypeptides prior to, and after incubation with MMP-1. We incubated 0.5 mL of 100 µM polypeptide in proteolysis buffer with 100 ng/mL of MMP-1 for 2 h at 25° C. The mass spectrometry data show that, after incubation, most of the 1.8 kDa MMP-sensitive peptide is cleaved off the 25.4 kDa ELP (FIG. 2). We also estimated the catalytic constant (kca) of MMP-1 in this buffer at 40° C. and the results are comparable to literature values for the same enzyme and substrate sequence (Patterson, J. & Hubbell, J. A. *Biomaterials* 2010, 31, 7836-7845). For example, an enzymatic reaction can be written in general form as:

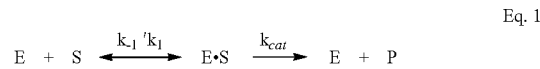

$$E + S \xrightleftharpoons[k_{-1}]{k_1} E \cdot S \xrightarrow{k_{cat}} E + P \qquad \text{Eq. 1}$$

In which E, S and P represent enzyme, substrate and product respectively. One of best-known models to describe enzymatic reactions in equilibrium is the Michaelis-Menten equation which relates the reaction rate to the substrate concentration:

$$v = \frac{d[P]}{dt} = \frac{V_{max} \cdot [S]}{K_M + [S]} \qquad \text{Eq. 2}$$

In this equation, $V_{max}$ is the maximum achievable rate at maximum substrate concentration and the constant $K_m$ is the substrate concentration at which half of the maximum rate is achieved. Since the maximum reaction rate is achieved when all the enzyme molecules are bound to the substrates, $V_{max}$ can also be written as (McDaniel, J. R. et al., *Biomacromolecules* 2010, 11, 944-952):

$$V_{max} = k_{cat} \cdot [E_t] \qquad \text{Eq. 3}$$

In which $E_t$ is the total enzyme concentration and kea is the catalytic constant or turnover number which is defined as the maximum number of substrate molecules converted to product per enzyme molecule in a given time.

A more useful form of Michaelis-Menten equation was derived by Lineweaver and Burke by rearranging equation Eq. 2:

$$\frac{1}{V_0} = \frac{1}{V_{max}} + \frac{K_M}{V_{max} \cdot [S]} \qquad \text{Eq. 4}$$

In which $V_0$ is the initial rate of the enzymatic reaction at a given substrate concentration. Using equation Eq. 4, we can calculate $V_{max}$ by plotting $1/V_0$ versus $1/[S]$ at different substrate concentrations and a constant enzyme concentration and then calculate $k_{cat}$ by implementing equation Eq. 3.

Figure 8:
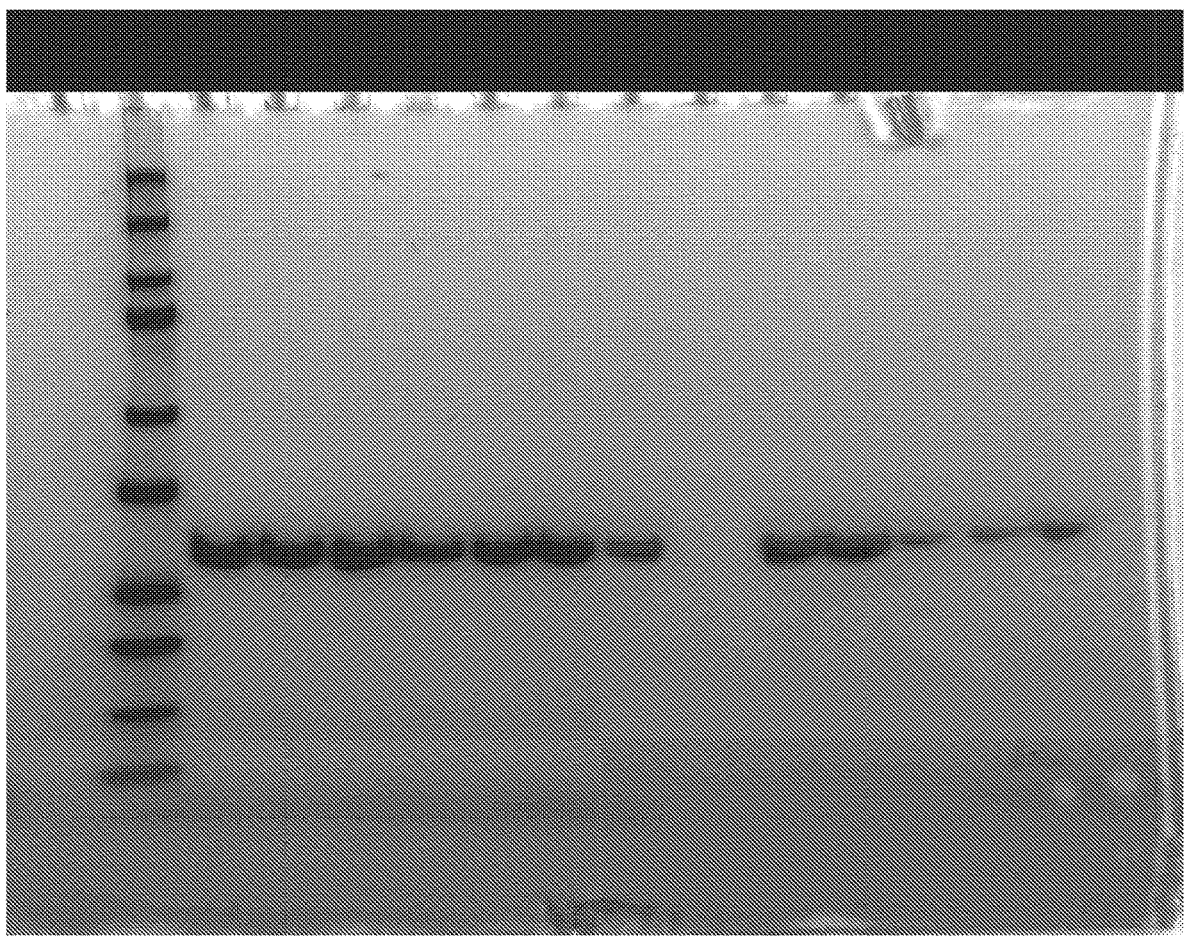
FIG. 8 shows an SDS-PAGE gel of solutions of 25 µL, 50 µL, 100 µL, 200 µL peptide-substrate in the buffer (lanes 1, 4, 7, and 10 respectively) and peptide-substrate solutions after 15 minutes (lanes 2, 5, 8 and 11) and after 30 minutes (lanes 3, 6, 9, and 12) of reaction with MMP-1 (20 ng/mL, 40° C.)

We performed a series of kinetic studies in which the concentration of the substrate in the buffer solution was chosen to be 25, 50, 100, and 200 µM. We then added 20 ng/mL of enzyme to each of the solutions and kept all the solutions at a constant temperature (40'C). After about 15 minutes we took a 50 µL sample from each of the solution. The samples were immediately supplemented with 50 nM protease inhibitor (N-Isobutyl-N-(4-methoxyphenylsulfonyl)glycyl hydroxamic acid; NNGH) to stop any further kinetic reaction. We then repeated the sampling at 30 minutes and subsequently ran all the samples along with the un-reacted samples on a SDS-PAGE gel (FIG. 8). The cleaved hydrophilic peptide is too small to be observed on the gel, but we can expect that with the progression of the enzymatic reaction, the cleavage of this short peptide will induce some small changes in the intensity of the peptide band on the gel. We quantified these changes by image analysis (ImageJ software) and used them to quantify the amount of product for each substrate concentration at each sampling time. We then calculated the initial rate of the reaction ($V_0$) by using the concentration of the converted substrate and the time of reaction.

Figure 9:
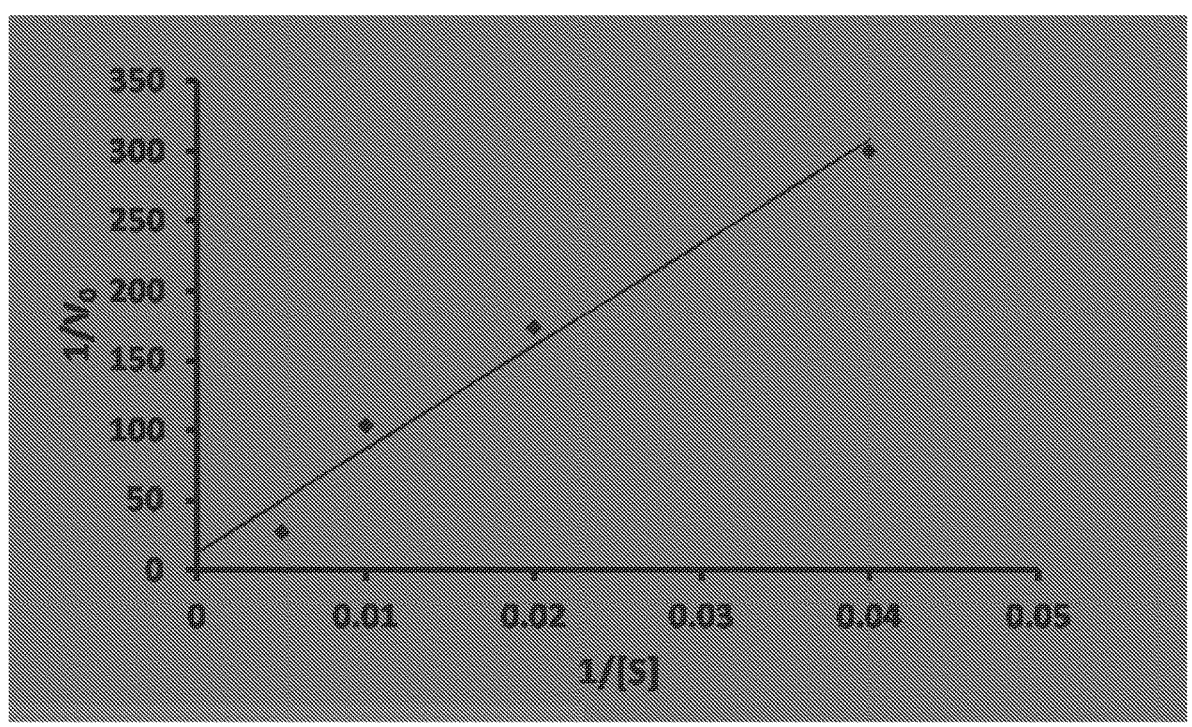
FIG. 9 shows a Lineweaver-Burke plot for different substrate concentrations (25, 50, 100, 200 µM) at constant enzyme concentration (20 ng/mL)

We then used equation Eq. 4 and plotted $1/[S]$ versus $1/[V_0]$ (FIG. 9) to calculate $V_{max}$. From $V_{max}$ and equation Eq. 3, we calculated $k_{cat}$ to be equal to 8.0±1.9 s$^{-1}$. This value is close to previously reported catalytic constant for this enzyme and the same substrate sequence at 37° C. in a slightly different buffer (5.25±0.95 s$^{-1}$) (Manafi, M. et al., *Microbiological Reviews* 1991, 55, 335-348).

Micelle Formation and Enzyme-Induced Aggregation.

FIG. 2 presents optical densities at 350 nm ($OD_{350}$) and hydrodynamic diameters of ELP-substrate fusion as a function of temperature prior to, and after, enzymatic reaction. The $OD_{350}$ of the ELP-substrate fusion before enzymatic reaction shows a small increase (about 0.2 OD units) as the solution is heated through the ELP's CMT (CMT: ≈38° C.). The particle size (hydrodynamic diameter) obtained from dynamic light scattering (DLS) from the solution of ELP-substrate fusion prior to enzymatic reaction also shows a significant change as the temperature of the solution is raised; below the CMT, the hydrodynamic diameter is <10 nm and above $T_t$, it is ≈50 nm. These changes are consistent with the self-assembly of ELP-substrate fusions (unimers) into micelles as the temperature is raised above the CMT (Ghoorchian, A. et al., *The Journal of Physical Chemistry. B* 2013, 117, 8865-8874). We note that there is a slight local maximum in both the optical density and hydrodynamic diameter at temperatures slightly above the CMT, which has been observed previously (Hassouneh, W., Duke University, PhD thesis, 2013); the origin of this small peak is, as yet, unclear.

After incubation of the ELP-substrate fusion with MMP-1 (100 ng/mL) for 12 h at 40° C., the optical density of the solution shows a dramatic increase as the solution is heated above the CMT to 45° C. The particles also show a large increase in size, from <10 nm in diameter to over a micron (i.e. to the upper detection limit of DLS at the measurement wavelength) at 38° C. The behavior of the product of the cleavage reaction is very similar to the temperature-induced bulk aggregation of a control ELP consisting solely of 60 repeats of (GVGVP)(SEQ ID NO:23)(Meyer, D. E. & Chilkoti, *A Biomacromolecules* 2004, 5, 846-851), which is almost identical in sequence to the ELP liberated after proteolysis of the ELP-substrate fusion (see FIG. 1).

These results strongly suggest that prior to incubation with MMP-1, the ELP-substrate fusion forms micelles at a temperature above its CMT of =38° C. (Ghoorchian, A. et al., *The Journal of Physical Chemistry. B* 2013, 117, 8865-8874). In contrast, after incubation with MMP-1, this construct forms large aggregates above ≈37° C., and its thermal behavior, is very similar to a control ELP that lacks the MMP-1 substrate and charged trailer peptide. Based on these results, we concluded that addition of MMP-1 to a solution of ELP-substrate fusion at a solution temperature above its CMT of 38° C. results in a transition from micelles with a low optical density to large micron-size aggregates with high optical density. We hypothesized that this drastic change in the solution (from clear to cloudy) could form the basis for a simple protease assay. We next examined this hypothesis by performing time-dependent studies of aggregation of the ELP-substrate fusion as a function of MMP-1 concentration at 40° C., a solution temperature above its CMT.

Time-Dependent Aggregation, Enzyme Detection and Quantification.

We examined the aggregation of the ELP-substrate fusion in proteolysis buffer (FIG. 4A) and in diluted human serum (FIG. 5A) upon addition of different concentrations of MMP-1 at temperatures above their CMT. We observed a gradual increase in the time that it takes for the solution to transition from low to high optical densities with decreasing enzyme concentration (FIG. 4A). In all cases, the aggregation process consists of at least two distinct phases: an initial small rate of increase in optical density, presumably due to incipient aggregation, followed by a much faster increase of optical density. To ensure that the increase in optical density and aggregation are the result of enzymatic cleavage of the ELP-substrate fusion by MMP-1, we performed a control experiment in which we added N-isobutyl-N-(4-methoxyphenylsulfonyl)glycyl hydroxamic acid (NNGH), an MMP-1 inhibitor, to the solution prior to the addition of 50 ng/mL MMP-1. We measured no significant change in optical density upon addition of the inhibitor, even after 900 minutes. By comparison, the same solution without the inhibitor formed aggregates in less than 50 min. To corroborate these results, we measured the changes in the particle size as a function of time in the presence of the enzyme (FIG. 4B) using DLS. These data show trends similar to those obtained by measurement of optical density.

We observed about 30 minutes of difference between the aggregation times obtained from DLS and optical density measurements for solutions containing 20 ng/mL of enzyme (FIGS. 4A, B). This difference might be due to a number of reasons. First, we measured optical density of the solutions on a temperature-controlled UV-vis spectrometer in which the temperature was kept constant and the optical density of the solution was measured every 3 seconds. On the other hand for dynamic light scattering, the instrument was programmed to measure the scattering of the solution at constant temperature (40° C.) at 5-minute time intervals. Each measurement was repeated three times and each one took about 2 minutes to complete. This introduced a time lag between the actual time of aggregation versus the time recorded by the instrument. The accumulation of these time lags can be the source of the observed difference between the two aggregation times. Second, it is possible that there was a slight temperature calibration difference between the two instruments that can cause some discrepancy between the two measurements. Regardless of the source of this discrepancy, it is important to note that our assay is based on the change in optical density, and not hydrodynamic radius, of solutions at a constant temperature. The light scattering experiment was only performed to better understand the process of micelle aggregation and is not intended for use as the primary assay technique.

Figure 4:
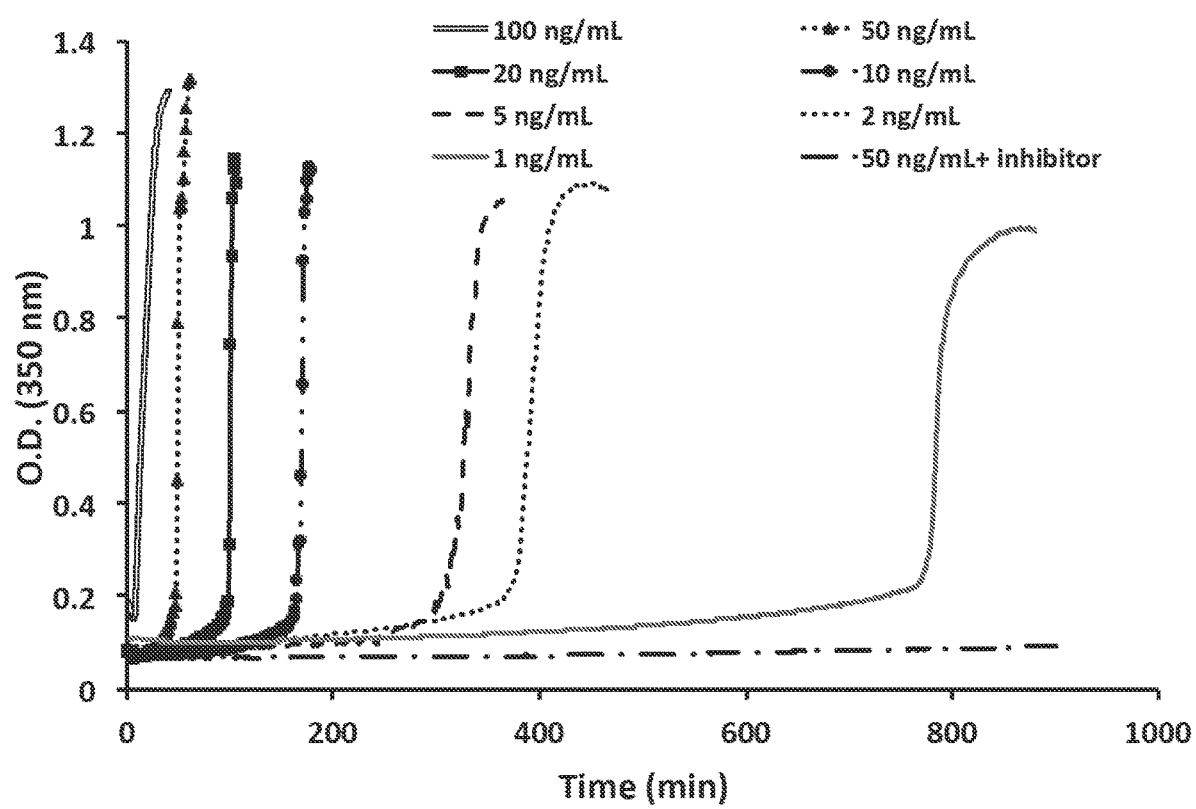
FIG. 4 shows optical density (A) and DLS measurements (B) as a function of time for ELP-substrate fusion (100 µM, 40° C.) in protease buffer at different MMP-1 concentrations. The black line in (A) shows the optical density of a suspension of ELP-substrate fusion (100 µM) in protease buffer in the presence of 50 ng/mL (2.5 nM) MMP-1 and 50 nM MMP-1 inhibitor. (C) Inverse aggregation time of ELP-substrate fusion (100 µM, 40° C.) in protease buffer as a function of MMP-1 concentration.
Figure 4:
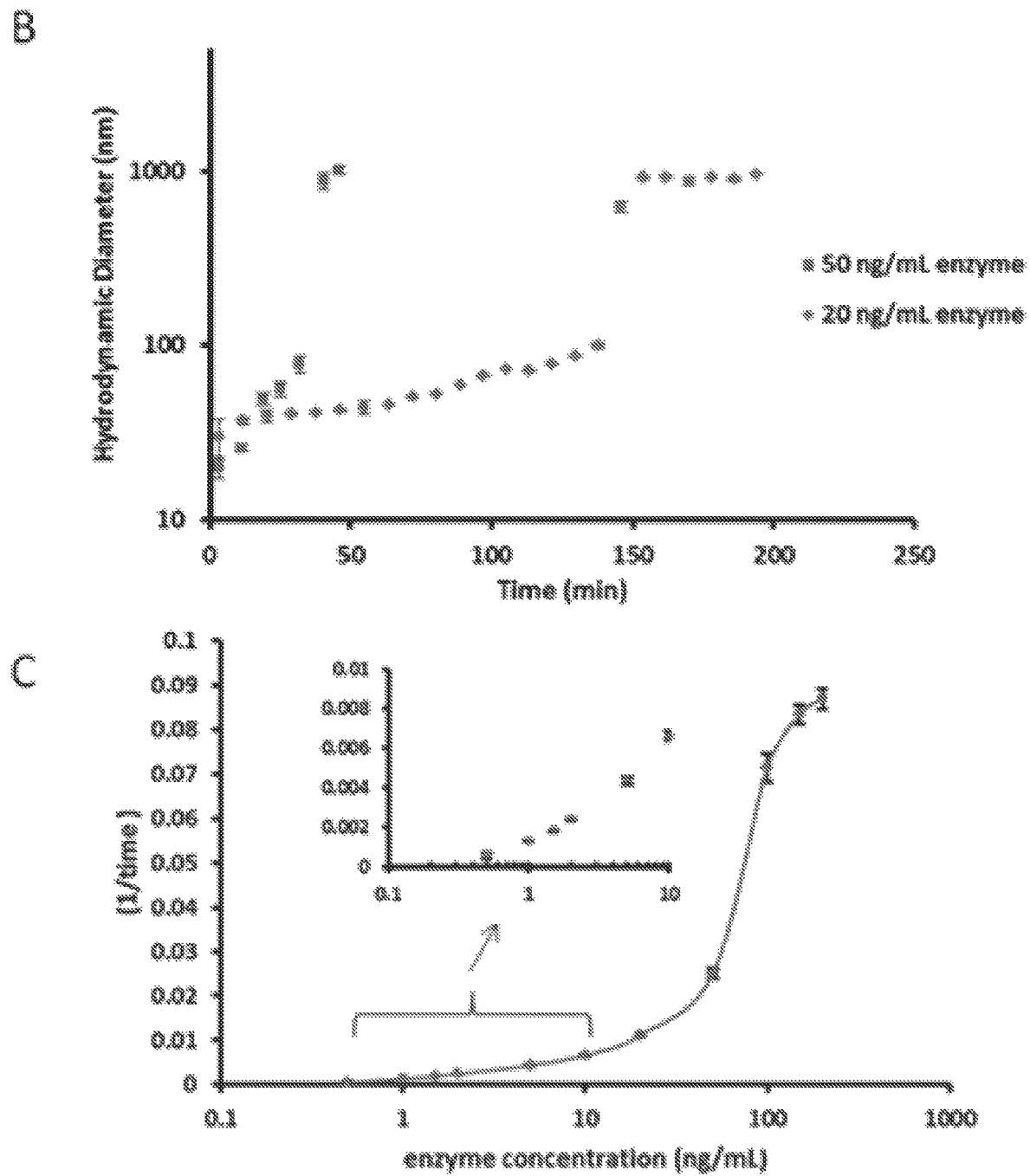
Figure 6:
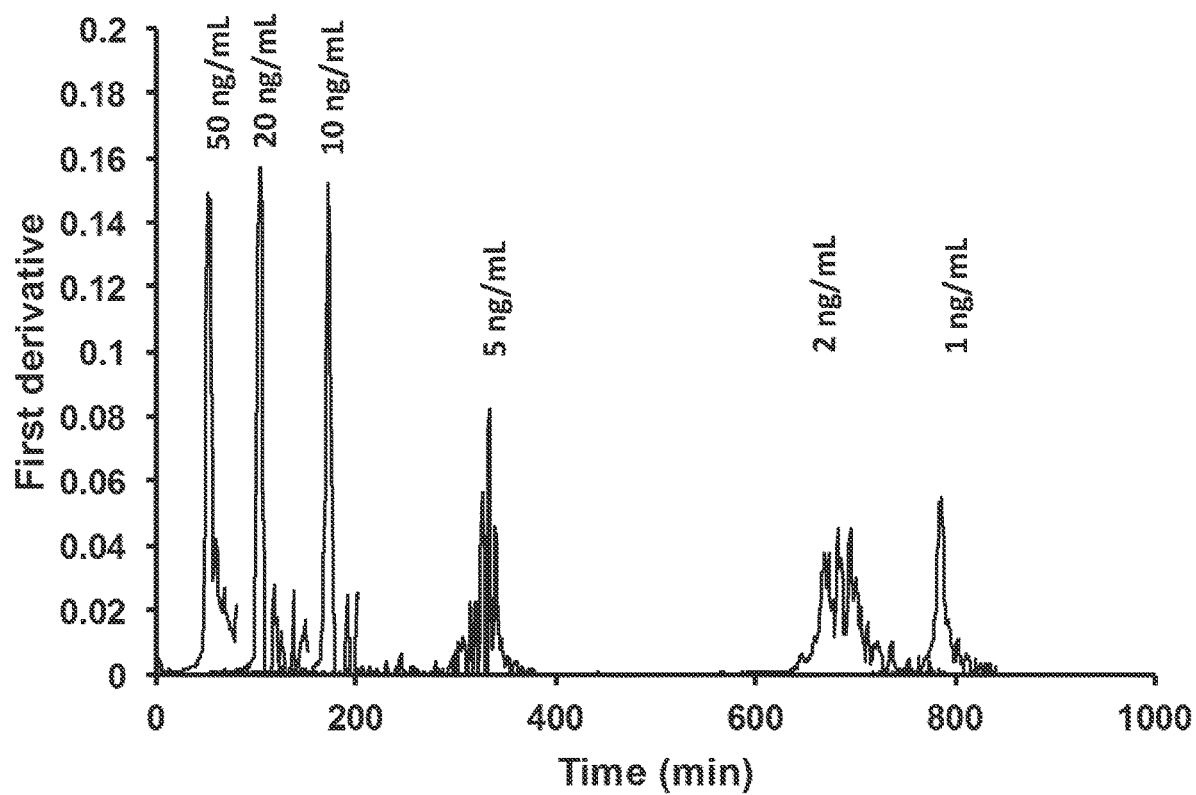
FIG. 6 shows first derivative of aggregation curves (optical density vs time) in buffer (from FIG. 4A) as a function of time. The time at which there is at least 100% increase in the slope of the optical density curve is considered the aggregation time. The aggregation times are plotted in FIGS. 4C and 5B for buffer assay and diluted serum, respectively.

We calculated the first derivative of each aggregation curve in FIG. 4 and found the time at which the slope shows at least 100% increase (see FIG. 6). This time, which we refer to as the aggregation time, is inversely proportional to the enzyme concentration and, by plotting the inverse of the aggregation time versus the corresponding enzyme concentrations, we obtain a sigmoidal assay response (FIG. 4C).

Figure 7:
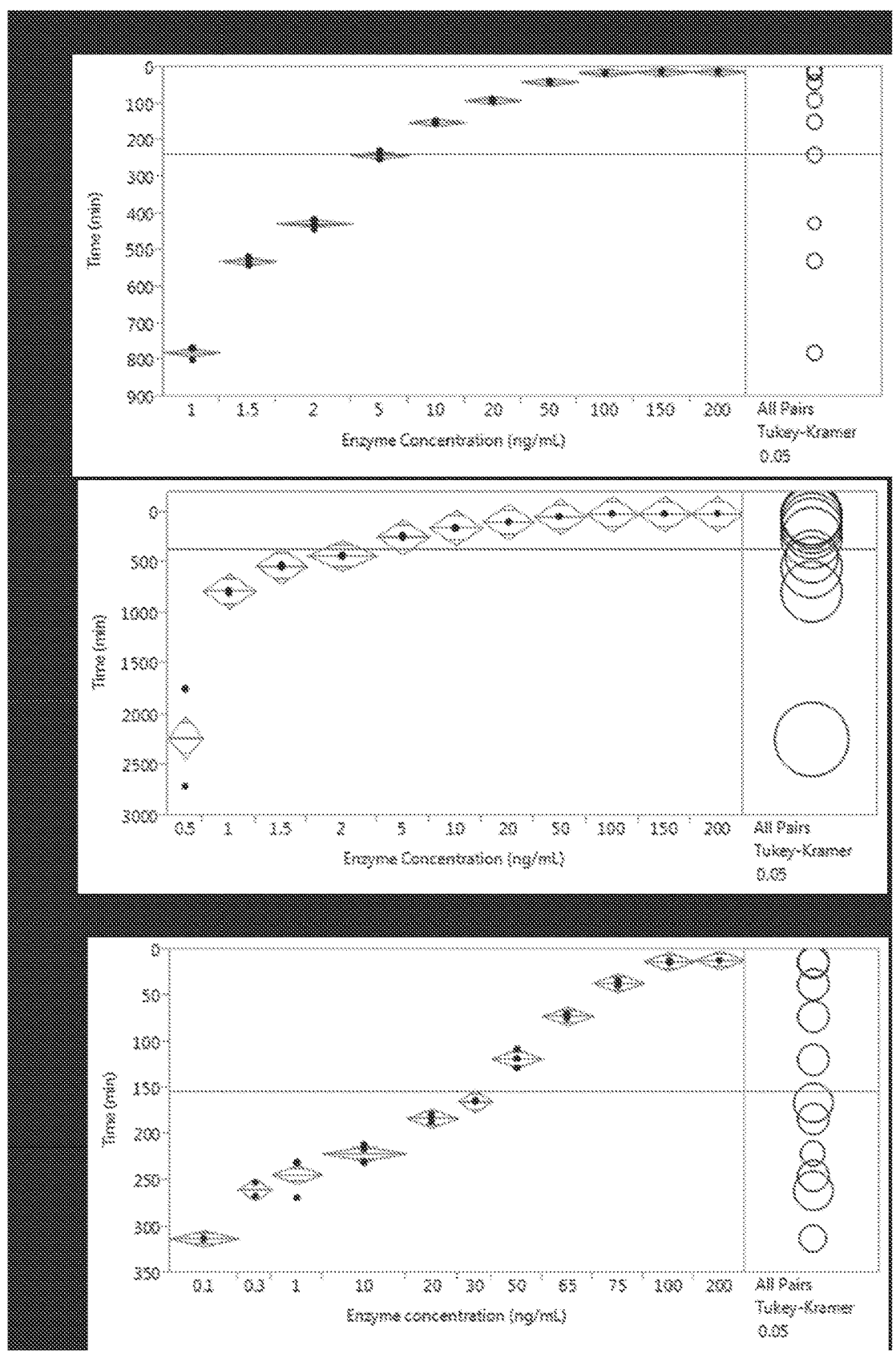
FIG. 7 shows ANOVA and All Pairs, Turkey HSD post-hoc test of aggregation times of a 100 µM assay solution in (A) buffer (from FIG. 4C) from 100 ng/mL to 1 ng/mL of protease, (B) in buffer from 100 ng/mL to 0.5 ng/mL of protease, and (C) serum (from FIG. 5B)

To calculate the limits of detection of the assay in buffer, we analyzed the data using ANOVA and an All Pairs, Turkey HSD post hoc test (JMP Pro Software, SAS). Based on this analysis, the assay becomes saturated above 100 ng/mL of enzyme (upper detection limit). The analysis also shows that the assay is statistically reliable down to 1 ng/mL of the enzyme (lower detection limit). Below this enzyme concentration (~0.5 ng/mL or lower), the measurements were not reproducible and resulted in statistically inconsistent data (see FIGS. 7A and B).

Figure 5:
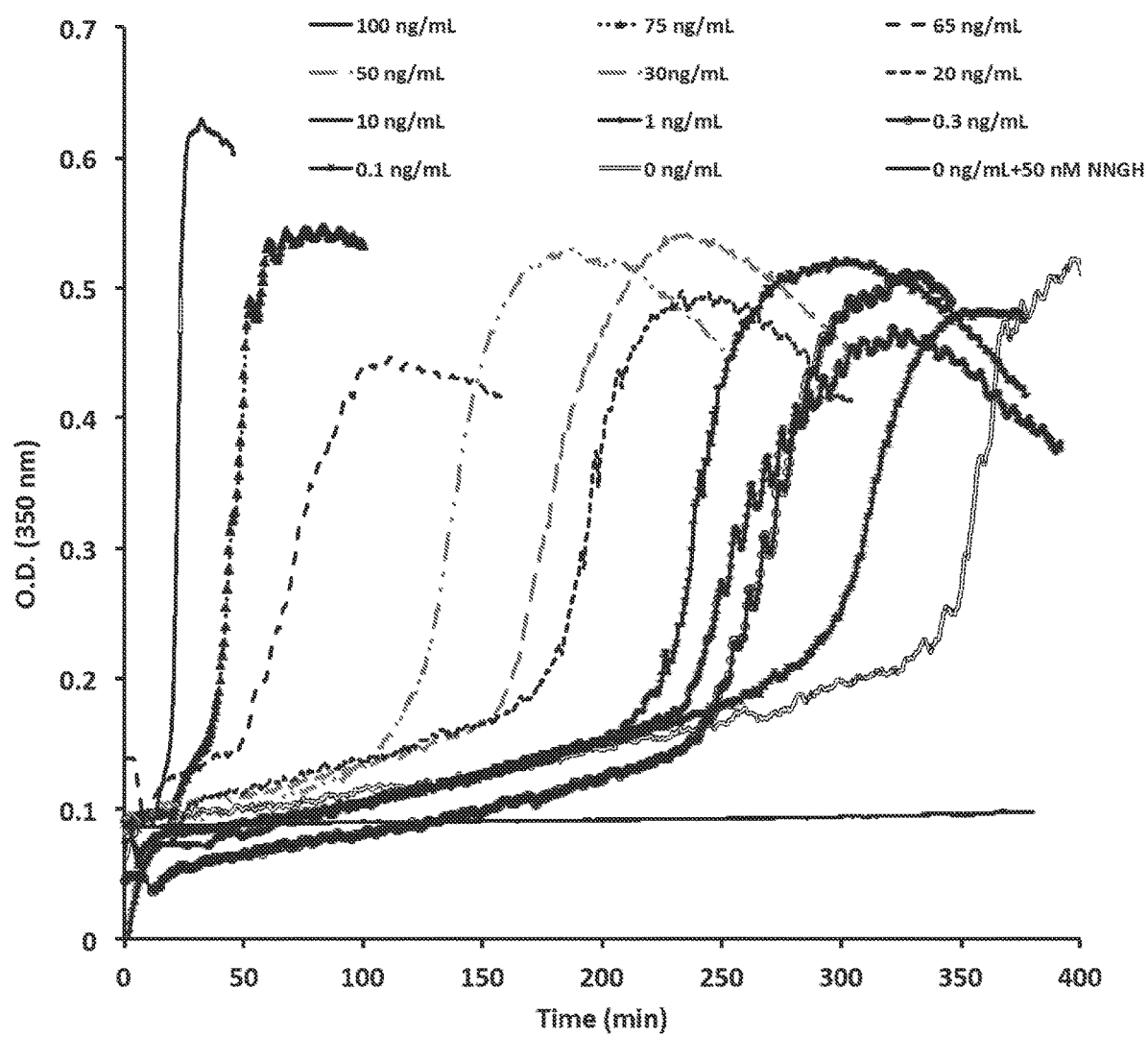
FIG. 5 shows: (A) Optical density as a function of time for solutions containing ELP-substrate fusion (100 µM, 37° C.) and diluted serum (40% in proteolysis buffer) incubated with different MMP-1 concentrations. (B) Inverse aggregation time as a function of MMP-1 concentration extracted from optical density curves in (A). Each aggregation time was calculated from the average of three separate measurements (C) Aggregation times in buffer (squares) and in diluted serum (diamonds). The data points shown by black triangles are the aggregation times in diluted serum, factoring the endogeneous enzyme concentration in the diluted serum, in addition to the added MMP-1 to the samples.
Figure 5:
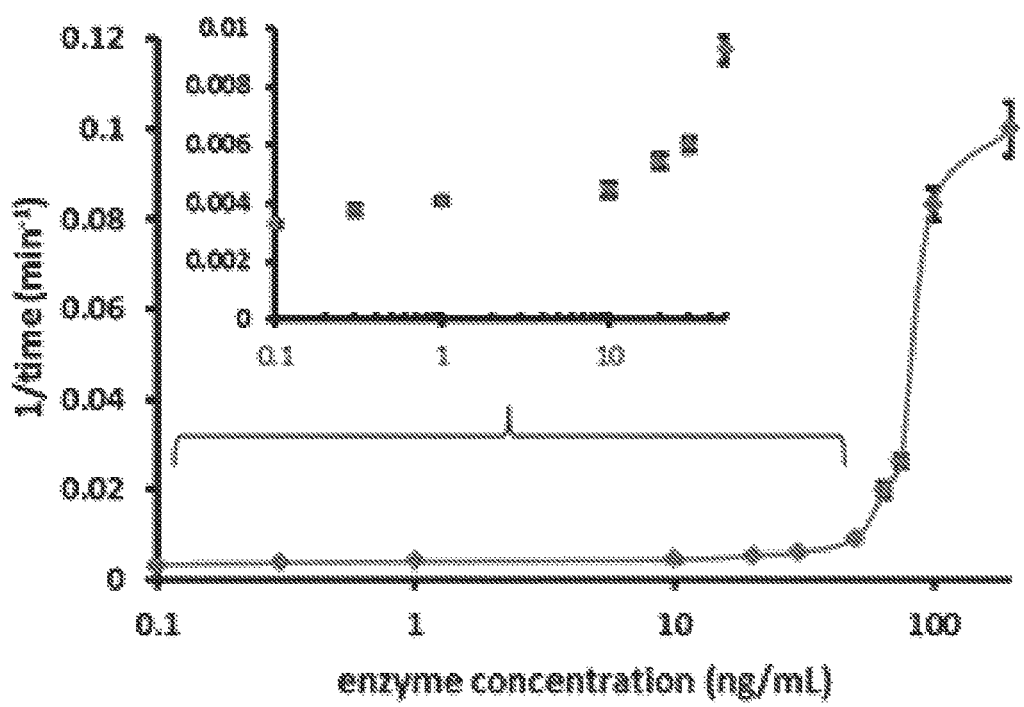
Figure 5:
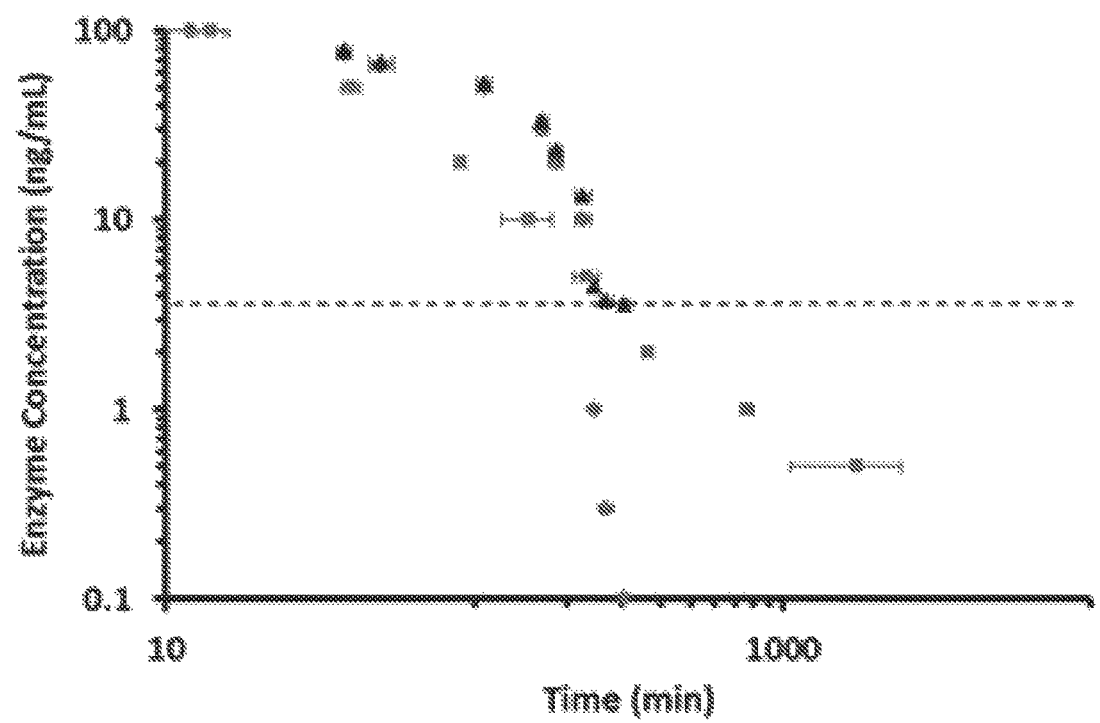

To examine the effect of MMP-1 concentration on aggregation time in solution conditions more relevant to clinical testing, we conducted the assay in a mixture containing the ELP-substrate fusion in 40% human serum in proteolysis buffer (which we refer to herein as diluted serum) at 37° C., which is above the CMT of the ELP-substrate fusion in this solution. We added varying quantities of MMP-1 to identical aliquots of diluted serum to obtain nominal MMP-1 concentrations between 0.1 ng/mL to 100 ng/mL and measured the change in optical density of these solutions over time (FIG. 5A). Below this concentration range the results were not reproducible and above this range, the aggregation was too fast to easily distinguish between different concentrations.

We observed a two-step aggregation process in diluted serum (FIG. 5A) similar to that noted for proteolysis in buffer, which suggests that the mechanism of cleavage and aggregation is similar in both cases. We plotted the inverse aggregation time as a function of enzyme concentrations in diluted serum and obtained the sigmoidal assay response similar to that for the assay in buffer (FIG. 5B). We also plot the enzyme concentration as a function of aggregation time to allow the enzyme concentration of an unknown sample to be directly read from its aggregation time (FIG. 5C). Unlike the assay in buffer, statistical analysis of the aggregation times of the assay in diluted serum cannot provide us with an intrinsic limit of detection (FIG. 7) due to to the presence of endogenous proteases in human serum.

To better understand the differences between the assay in buffer and in diluted serum, we compared the aggregation times for the assay in the two media (FIG. 5C). The assay shows slightly different aggregation times and trends in the enzyme concentration range from 100 ng/mL to about 5 ng/mL. These differences may be due to the presence of other modulators-proteases or inhibitors—of MMP-1 activity in human serum tested. Below 5 ng/mL, the assay in diluted serum shows markedly shorter aggregation times compared to the assay in buffer. This is likely due to the presence of active MMP-1 in the human serum used in these experiments. The level of endogenous MMP-1 in healthy human serum has been shown to be about 1 to 3 ng/mL (Young-Min, S. A. et al., *Annals of the Rheumatic Diseases* 2001, 60, 846-851). Existence of this amount of enzyme in the serum solution can noticeably change the aggregation time of solutions that are doped with similar concentrations of MMP-1 (1 to 5 ng/mL). To further confirm the existence of endogenous MMP-1 in the serum solution in these experiments, we measured the change in optical density of the ELP-substrate fusion in diluted serum with no added MMP-1 and observed aggregation after ~350 min. We then ran diluted serum with added MMP-1 inhibitor (NNGH), but without any added MMP-1 and observed no aggregation after 400 minutes (FIG. 5A). This indicates that the aggregation of the diluted serum and ELP-substrate fusion with no added MMP-1 was indeed the result of the presence of trace MMP-1 in the serum sample and that is the likely reason for the difference between the aggregation times in the buffer and diluted serum samples.

It is notable that, to the best of our knowledge, all MMP-substrate peptides are shown to have some sensitivity towards a number of MMPs and not exclusively a single protease. In addition, most of the MMP inhibitors (including NNGH) are reported to inhibit groups of MMPs. This introduces a potential inherent limitation on any peptide-based MMP assay. We believe that this may also be true for the peptide used in this study and MMPs other than MMP-1 in the serum samples may have contributed to peptide cleavage. While we may expect some nonspecific cleavage of the peptide in human serum, because the peptide is optimized as a substrate for MMP-1 (Patterson, J. et al., *Biomaterials* 2010, 31, 7836-7845; Turk, B. E. et al., *Nature Biotechnology* 2001, 19, 661-667), we expect that most of the peptide cleavage to be the result of the added MMP-1 to the sample and the endogenous MMP-1 in the human serum sample rather than other MMPs. Thus, although we cannot entirely rule out the possibility of the effect of other MMPs in the cleavage of the peptide, we expect their effect to be minimal in comparison to that of MMP-1. It is important to note that, in this study, we used MMP-1 to prove the concept of our protease assay system, and that the flexible, modular design of our system allows use any other protease-sensitive peptide in its design.

To account for the presence of MMP-1 protease in human serum, we conducted linear regression of the aggregation time in diluted serum from 100 to 10 ng/mL of enzyme and extrapolated to estimate the concentration of protease that would result in an aggregation time of 350 min. In this manner, we estimated the baseline protease concentration in diluted serum to be 3.5 ng/mL (dotted line in FIG. 5C), which is consistent with the reported endogenous MMP-1 in healthy serum. By adding this value to each dilute serum data point in FIG. 5C (diamonds), we obtained a corrected data set that is more consistent with the aggregation times obtained from the assay in buffer (triangles).

Despite the complicating factors discussed above and considering that healthy human serum may contain between 1.5 to 3 ng/mL of MMP-1, the dynamic range of our assay system in serum (from the baseline endogenous MMP-1 level in human serum of about 3 ng/mL to 100 ng/mL) and in buffer (1 ng/mL to 100 ng/mL) is quite wide and easily encompasses the physiological range for MMP-1 during many diseases including metastatic melanoma (>30 ng/mL), lung cancer (3 ng/mL to 8 ng/mL) (Li, M. et al., *Lung Cancer* 2010, 69, 341-347) and dilated cardiomyopathy (5 ng/mL to 6 ng/mL) (Schwartzkopff, B. et al., *European Journal of Heart Failure* 2002, 4, 439-444). The limit-of-detection and dynamic range of this assay is comparable to those of commercially available MMP-1 assays from companies such as Abnova (0.15 ng/mL to 10 ng/mL) (Lowe, S. B. et al., *Acs Nano* 2012, 6, 851-857), GE healthcare (6.25 ng/mL to 100 ng/mL) (Elkington, P. T. G. et al., *Clinical and Experimental Immunology* 2005, 142, 12-20), and Millipore (0.023 ng/mL to 3.6 ng/mL) (Karapanagiotidis, G. T. et al., *Journal of Cardiothoracic Surgery* 2009, 4, 59). Further testing with biological samples that are scrupulously free of MMP-1 may determine the true limit-of-detection of our assay in serum.

CONCLUSIONS

We have developed a homogeneous assay for MMP-1 using an engineered stimulus-responsive polypeptide consisting of an ELP fused to an MMP-1 substrate and a charged, hydrophilic peptide. We showed that this ELP-substrate fusion forms micellar nanoparticles when heated above its CMT. Exposure to MMP-1 results in cleavage of the hydrophilic coronae of these micelles and the formation of larger micron size aggregates. As the rate of peptide cleavage is a function of the enzyme concentration, the time that it takes for the micelles to aggregate into large particles can be correlated to the protease concentration in solution. The detection limit of the assay is comparable to many of the commercially available MMP-1 assays. This assay however has some distinct advantages that include: (i) its simplicity, (ii) the fact that it does not require sophisticated instrumentation and can even be conducted by visual inspection, and (iii) the fact that the output of the assay is simply the time of aggregation, which can then be easily correlated to the enzyme concentration using a calibration curve. These features may make this new assay useful for routine testing of patients in point-of-care (POC) settings. This can be particularly useful in areas that are particularly susceptible to certain diseases like infectious diseases and in which may lack the resources of full diagnostic laboratories. Such low cost, portable POC devices can be used as the first stage of diagnosis without the need for trained specialists. It may also be in high throughput drug discovery applications. We note that this assay format is not restricted to MMP-1, but can easily be extended to a wide range of proteases, as well as other enzymes of biomedical interest such as kinases and phosphatases that result in modification of the phase behavior of engineered stimuli-responsive polypeptides.

Example 2

In the present example, the enzyme-sensitive peptide is located in between two blocks of a micelle-forming block copolymer. This approach would be specifically useful for systems in which the protease-sensitive peptide is highly insoluble, but it can also be used for soluble peptide sequences as well. The exemplary case here is based on using the same MMP-1 sensitive peptide as described in Example 1, but the concept can easily be adapted to other peptides and other proteases as well.

Figure 10:
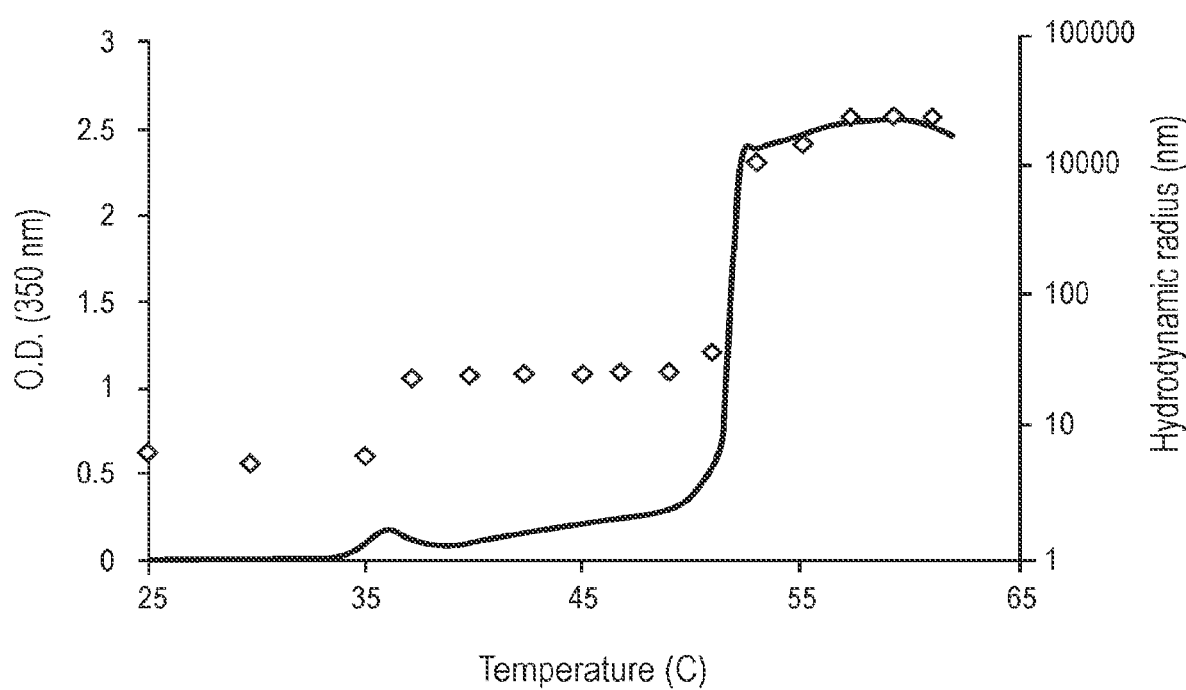
FIG. 10 shows optical density (solid line) and hydrodynamic radius (diamonds) of a 100 µM solution of polypeptide in buffer (HEPES, 50 mM; $CaCl_2$, 10 mM; $MgCl_2$, 0.5 mM, $ZnSO_4$, 50 µM) as a function of temperature. Both UV absorbance and dynamic light scattering show two transitions. The first one is from monomers to micelles and the second one from micelles to aggregates. The temperature of the first transition is just above 35° C. and the temperature for the second one is about 50° C.
Figure 11:
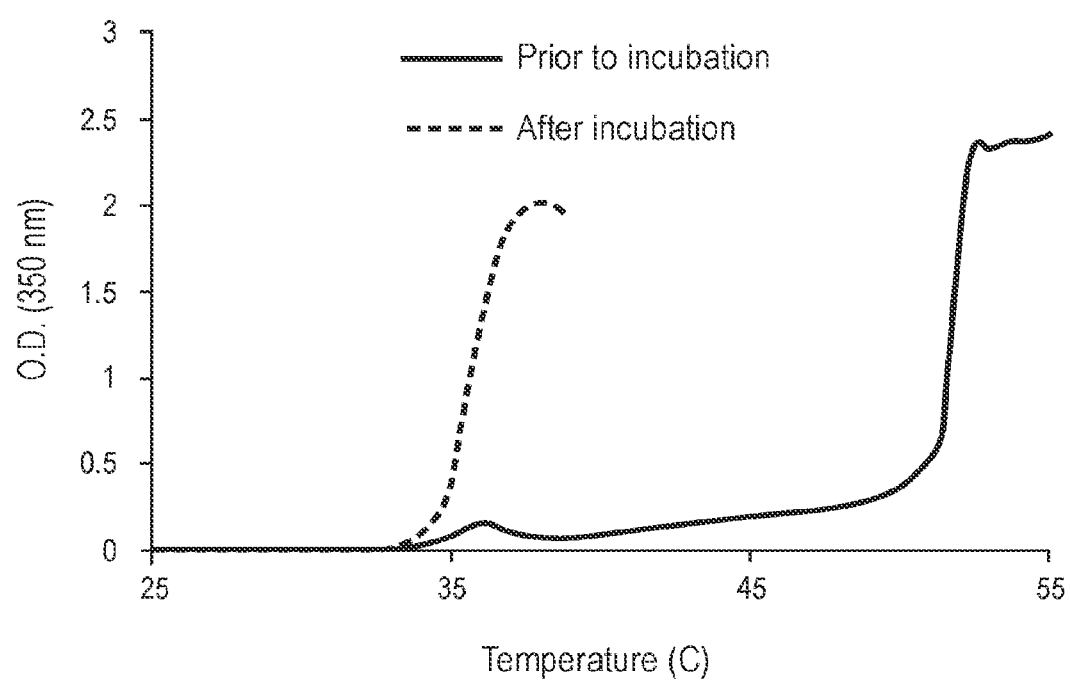
FIG. 11 shows optical density versus temperature of a 100 µM peptide solution before addition of MMP-1 enzyme (solid line) and after incubation with 100 ng/ml of enzyme for 2 hours (dashed line). The drastic change in aggregation temperature is a result of separation of the two segments of the micelle-forming block as a result of enzymatic digestion. The temperature at which aggregation occurs after the digestion is the same as the micelle forming temperature prior to enzymatic reaction.
Figure 12:
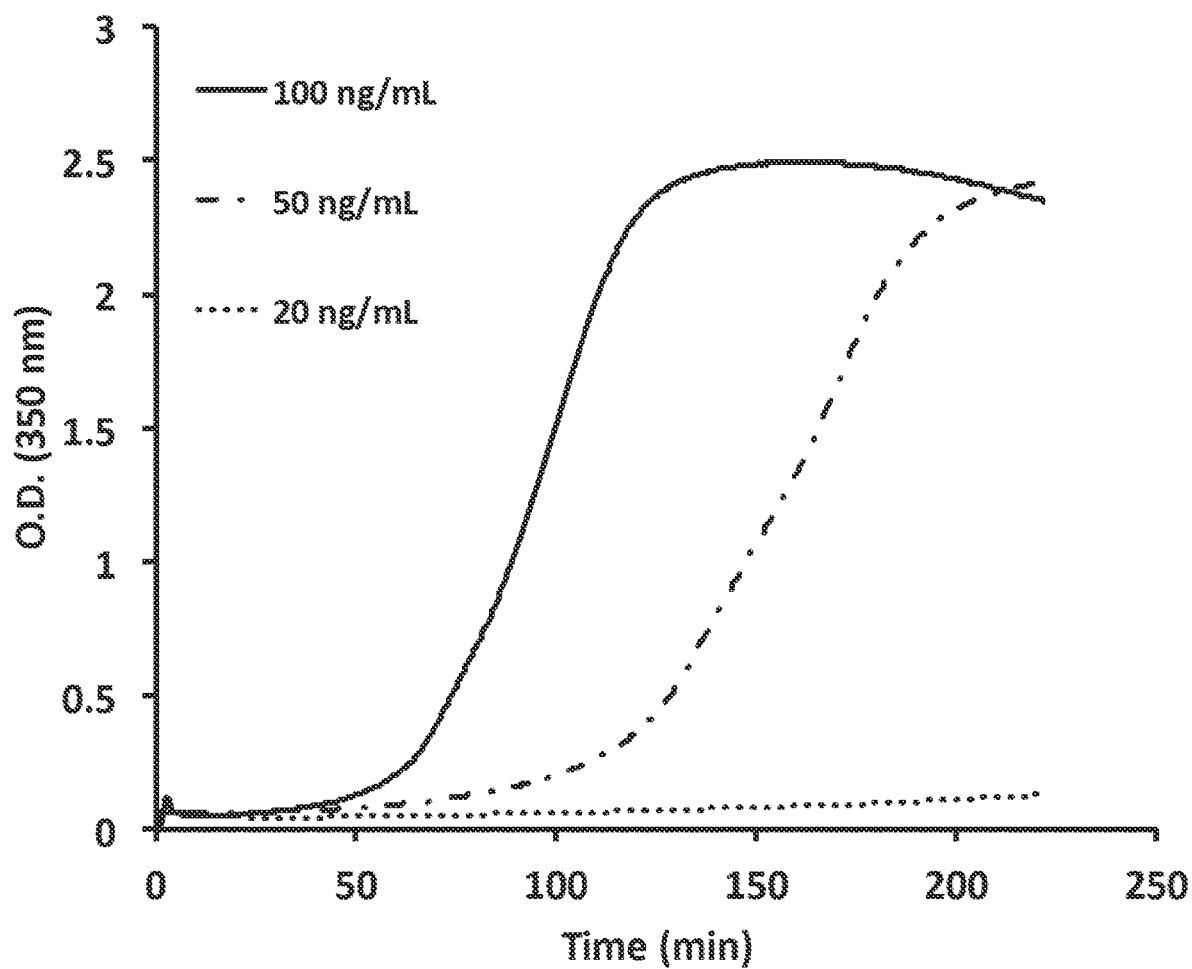
FIG. 12 shows optical density versus time for identical solutions containing 100 µM peptide, in buffer incubated at 37° C. with different enzyme concentrations.

All the materials, methods, and experimental processes were similar to those described in Example 1 unless otherwise specified. The gene was designed to encode a fusion polypeptide having the final sequence of: MSKGPGWGVG (VPGVG)$_{60}$GDGQVPMSMRGGDDEG QQDDEE(VPGAGVPGGG)$_{30}$YG (SEQ ID NO:2). In this sequence, the MMP-1 sensitive peptide (GDGQVPMSMRGG; SEQ ID NO:3) is located in between the hydrophobic ELP tail ((VPGVG)$_{60}$; SEQ ID NO:4) and a long hydrophilic peptide sequence ((VPGAGVPGGG)$_{30}$; SEQ ID NO:5). The combination of these hydrophobic and hydrophilic ELPs, without the protease sensitive enzyme, is shown previously to make micelles above the transition temperature of hydrophobic tail (Hassouneh, W. et al., *Biomacromolecules* 2012, 13, 1598). Because of the short length of the added protease-sensitive peptide between the two segments of this block copolymer, the micelle formation characteristics of the block copolymer does not change, and two transition temperatures are observed for this tri-block peptide as well (FIG. 10). Incubation of these micelles with MMP-1 enzyme is shown to result in drastic changes in optical densities at the micelle-forming transition temperature (FIG. 11). This is the result of the digestion of MMP-sensitive peptide as described in Example 1. Using this change in solution behavior, we also showed that incubation of similar solutions with different amount of enzyme, results in different aggregation time the same way as described in Example 1 (FIG. 12). The aggregation time can then be used in a similar fashion to quantify the enzyme in an unknown solution.

Figure 13:
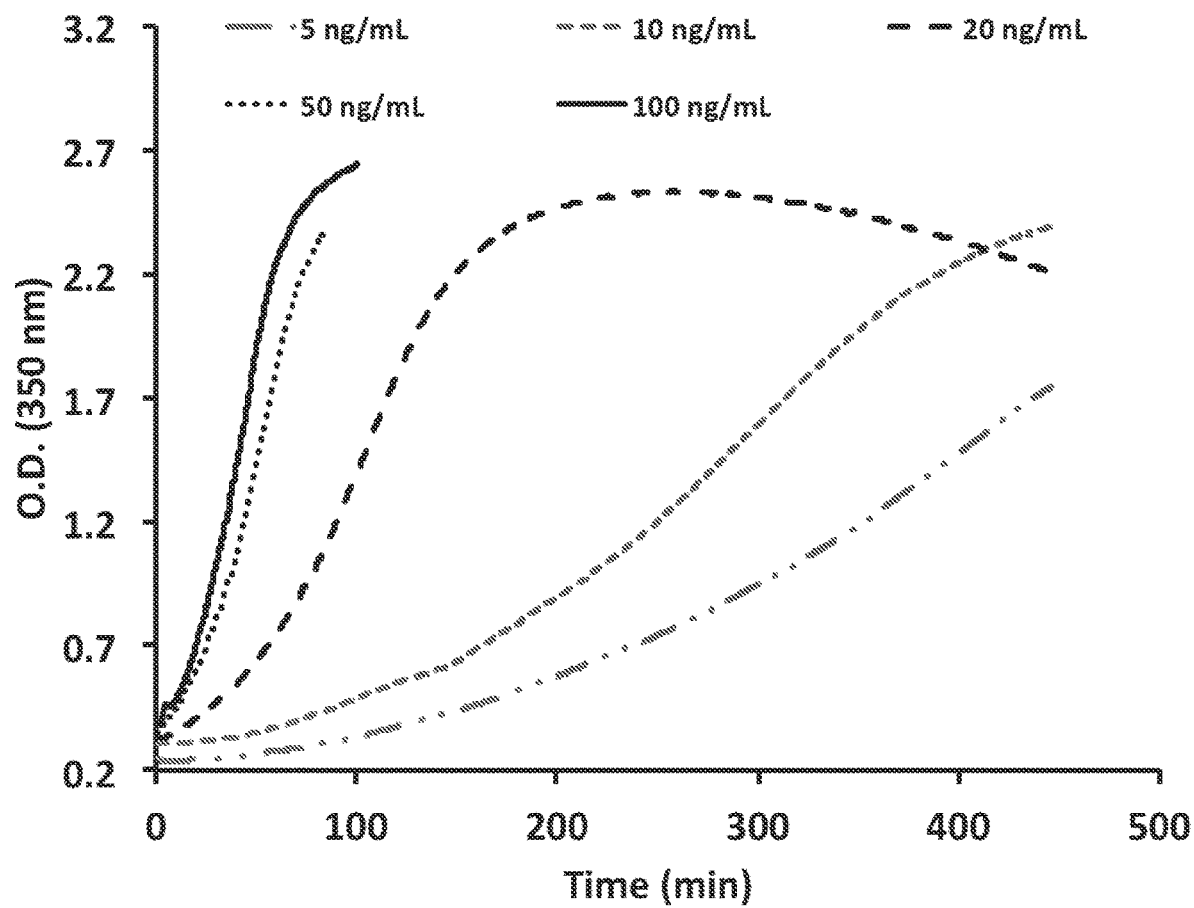
FIG. 13 shows optical density versus time for solutions containing 100 µM of micelle-forming peptide and 8 µM of (VPGVG)$_{60}$ (SEQ ID NO:4). Mixing of the micelle-forming peptide and hydrophobic peptide is shown to considerably increase the rate of aggregation.

In this system, we were also able to decrease the aggregation time, and consequently decreased the total assay time, by mixing the micelle-forming solution with a small amount of hydrophobic peptide (VPGVG)$_{60}$ (SEQ ID NO:4). The presence of small amount of hydrophobic peptide accelerate the bulk aggregation by providing more hydrophobic chains as the digestion goes on in the solution (FIG. 13).

This example shows the flexible nature of the system and how it is possible to adapt it to different designs, based on the requirements and limitations of each specific protease.

Example 3

The present example demonstrates the use of other protease-sensitive peptides within the micellar format of the assays described above. Prostate Specific Antigen (PSA) is a glycoprotein enzyme encoded in humans by the KLK3 gene. It is mainly secreted from prostate gland and it has been shown that high concentration of PSA in blood serum, urine, or other bodily fluids can potentially be used as a biomarker to distinguish men with high risk of prostate cancer from healthy men. In the present example, we demonstrated that we can use the micelle-based protease detection system described above to detect and quantify active PSA in bodily fluids. One of the advantages of this system is that we were able to quantify active PSA instead of total PSA; a feature that may have clinical significance.

Figure 14:
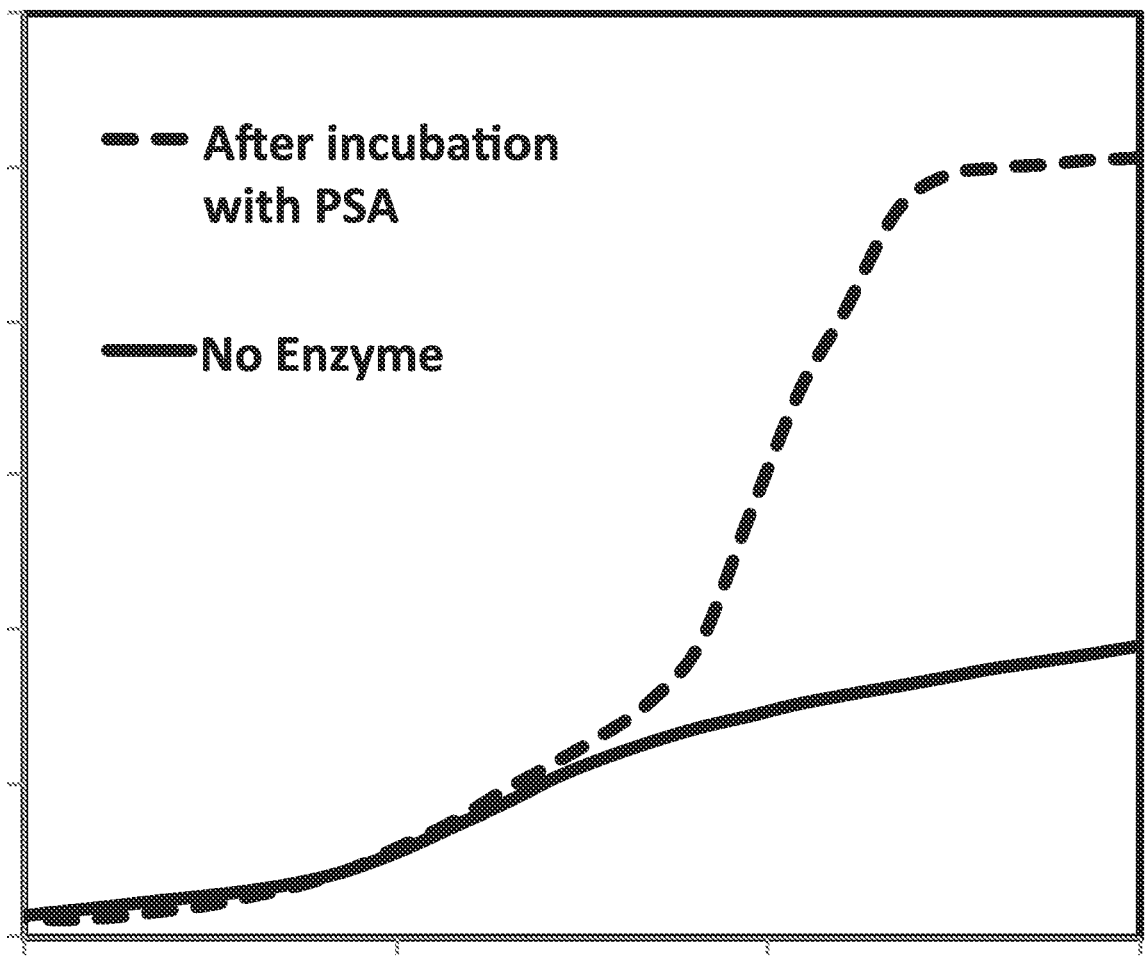
FIG. 14 shows optical density measurements of 100 µM solution of "PSA peptide" prior to and after incubation with 20 ng/mL active PSA in protease buffer at 37° C. for 2 hours. The graph clearly shows the increase in optical density of the solution above the transition temperature after incubation with enzyme.

We designed a number of genes and replaced the MMP-1 sensitive peptide described above with a PSA-sensitive peptide sequence. One such example is: M(GVGVP)$_{60}$GDGQSSIYSQTEEQQDDEEG (SEQ ID NO:6; referred to herein as PSA peptide). Optical density measurements of 100 µM solution of PSA peptide were obtained prior to and after incubation with 20 ng/mL active PSA in protease buffer at 37° C. for 2 hours. FIG. 14 shows a distinct difference in the presence of active PSA, with an increase in optical density of the solution above the transition temperature after incubation with enzyme. The data showed that the assay system is flexible enough to easily be adapted to other protease biomarkers, in this case PSA.

Example 4

The present example demonstrates the use of other environmentally-responsive polymers and biopolymers within the presently disclosed assays. In the previous examples, elastin-like polypeptides (ELPs) were used as the temperature-responsive biopolymer in the system. ELPs belong to a family of polymers with lower critical solution temperature (LCST) behavior. These polymers are soluble below a transition temperature but become insoluble when heated above their LCST. As shown in previous examples, this behavior can be very useful in our protease detection assays. However, the flexible and modular design of the presently disclosed molecular system lets us use other environmentally-responsive polypeptides with very different behaviors.

Figure 15:
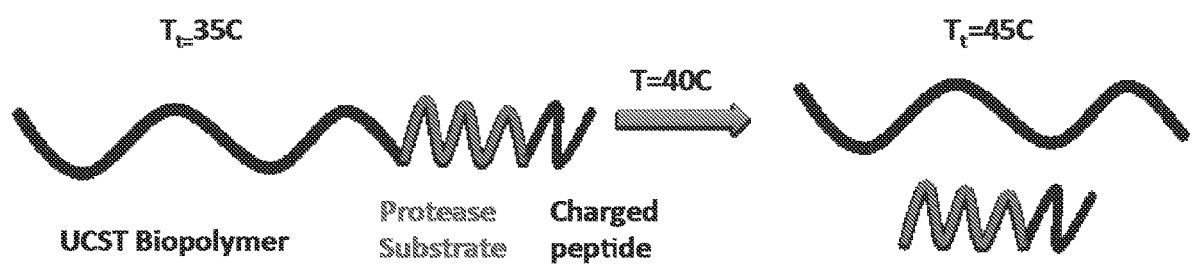
FIG. 15 shows a schematic of upper critical solution temperature (UCST) biopolymer cleavage and the subsequent change in transition temperature.

For example, polymers that show upper critical soluble temperature (UCST) behavior are shown to behave opposite of LCST polymers in many respects. Most basically, UCST polymers are insoluble below a transition temperature and can become soluble above their UCST (FIG. 15).

To exemplify the use of UCST peptides, we changed our system by incorporating a number of UCST biopolymers with the MMP-1 substrate, for example: M(YPSDGRGQ)$_{40}$YGDGQ VPM SMRGGDEGQQDDEEGY (SEQ ID NO:7; referred to herein as the A4 construct). Cleavage of the protease-sensitive peptide between S and M in this sequence at a constant temperature would increase the transition temperature, which can cause the solution to transition from clear to cloudy. The time that takes for the transition to happen depends on the enzyme concentration similar to in the manner in which the LCST, micellar-based assays described above function.

Figure 16:
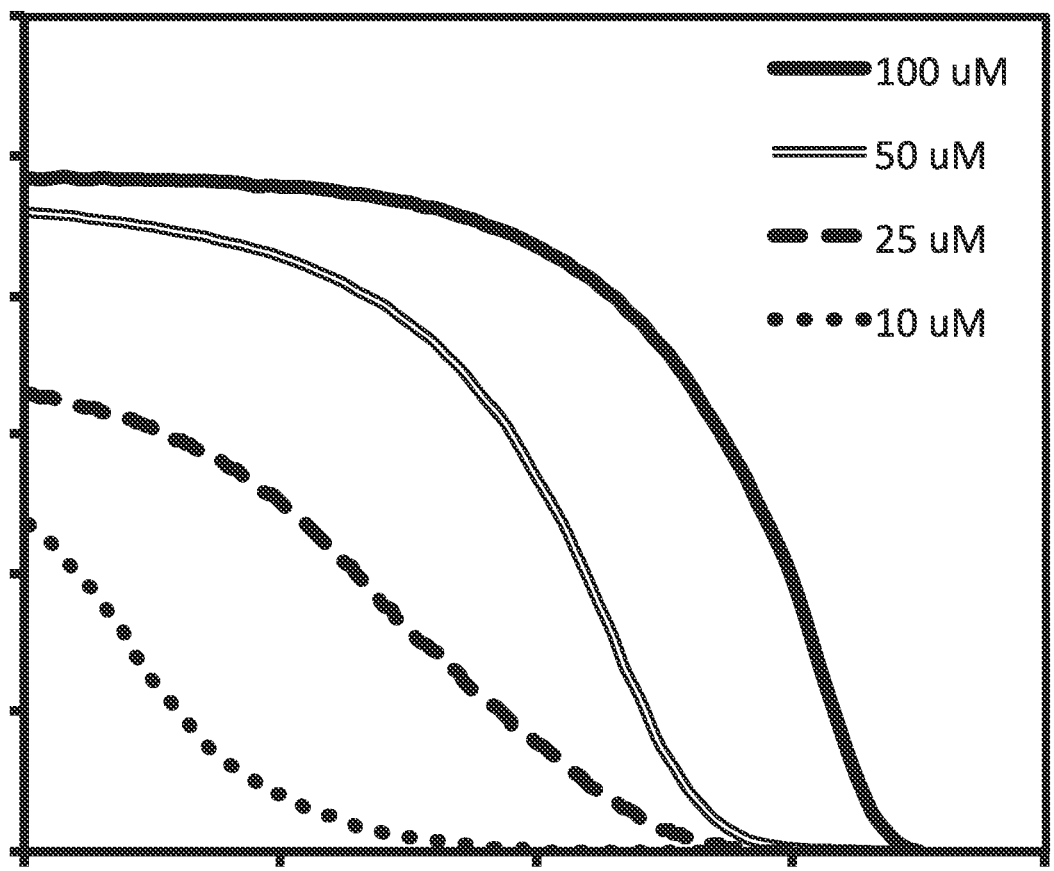
FIG. 16 shows thermo-responsive behavior of the A4 construct (a MMP-sensitive-UCST biopolymer) at different A4 concentrations. In contrast to ELP-based constructs, which exhibit lower critical solution temperature (LCST) behavior, the transition temperature of these biopolymers shifts to higher temperatures as the solution concentration increases.
Figure 17:
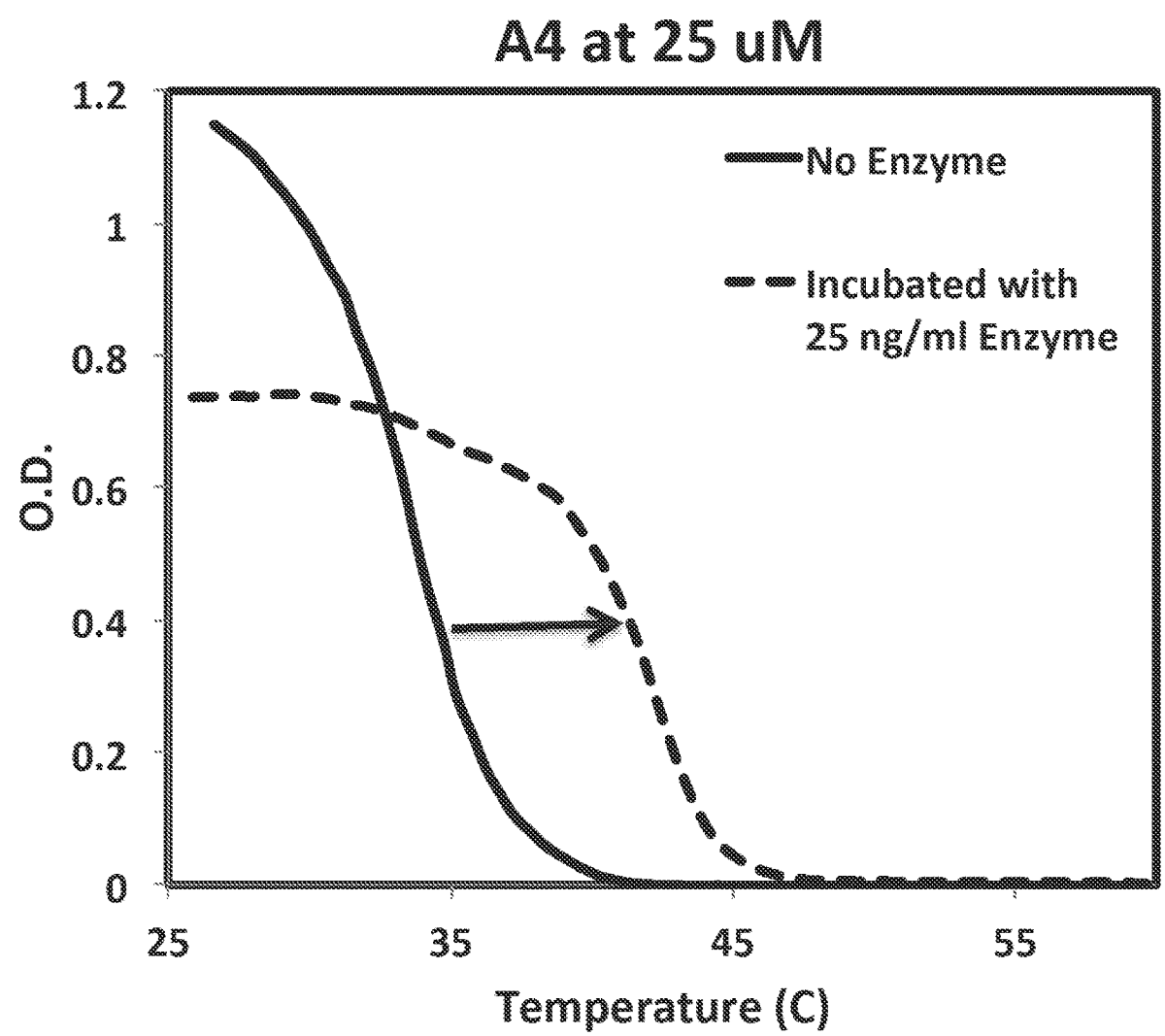
FIG. 17 shows a change in transition temperature of the A4 construct at 25 µM prior to (solid line) and after (dashed line) incubation with 25 ng/mL of MMP-1 enzyme at 37° C. The change in transition temperature shows the effect of cleaving the MMP-1 substrate.

For example, FIG. 16 shows the thermo-responsive behavior of the A4 construct (a MMP-sensitive-UCST biopolymer) at different A4 concentrations. In contrast to ELP-based constructs, which exhibit LCST behavior, the transition temperature of these biopolymers shifts to higher temperatures as the solution concentration increases. As shown in FIG. 17, a change in transition temperature of A4 construct at 25 µM prior to (solid line) and after (dashed line) incubation with 25 ng/mL of MMP-1 enzyme at 37° C.

Figure 18:
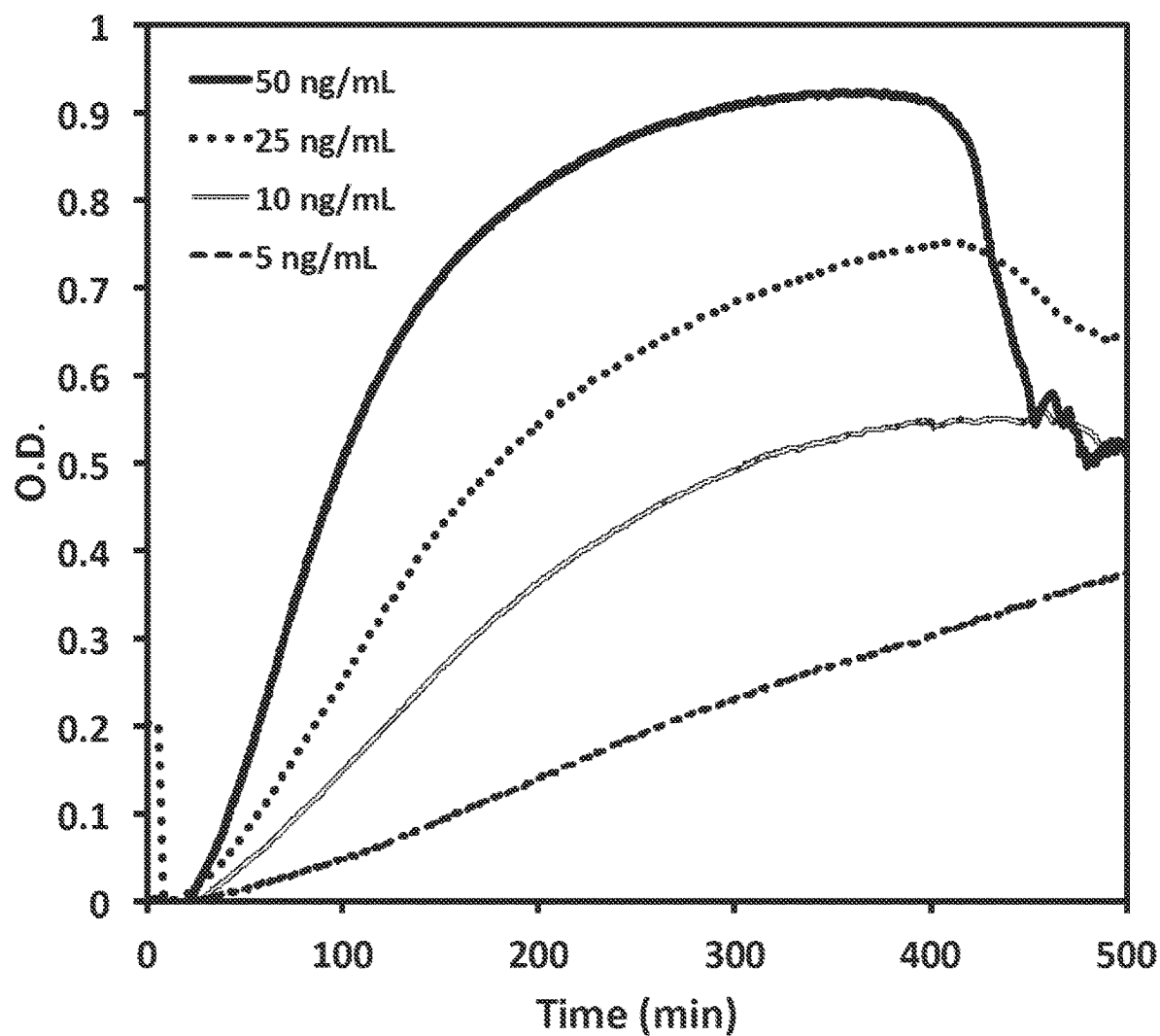
FIG. 18 shows optical density of the A4 solution at 50 µM and 40° C. as a function of time. The solutions become cloudy at different times depending on the concentration of MMP-1.
Figure 19:
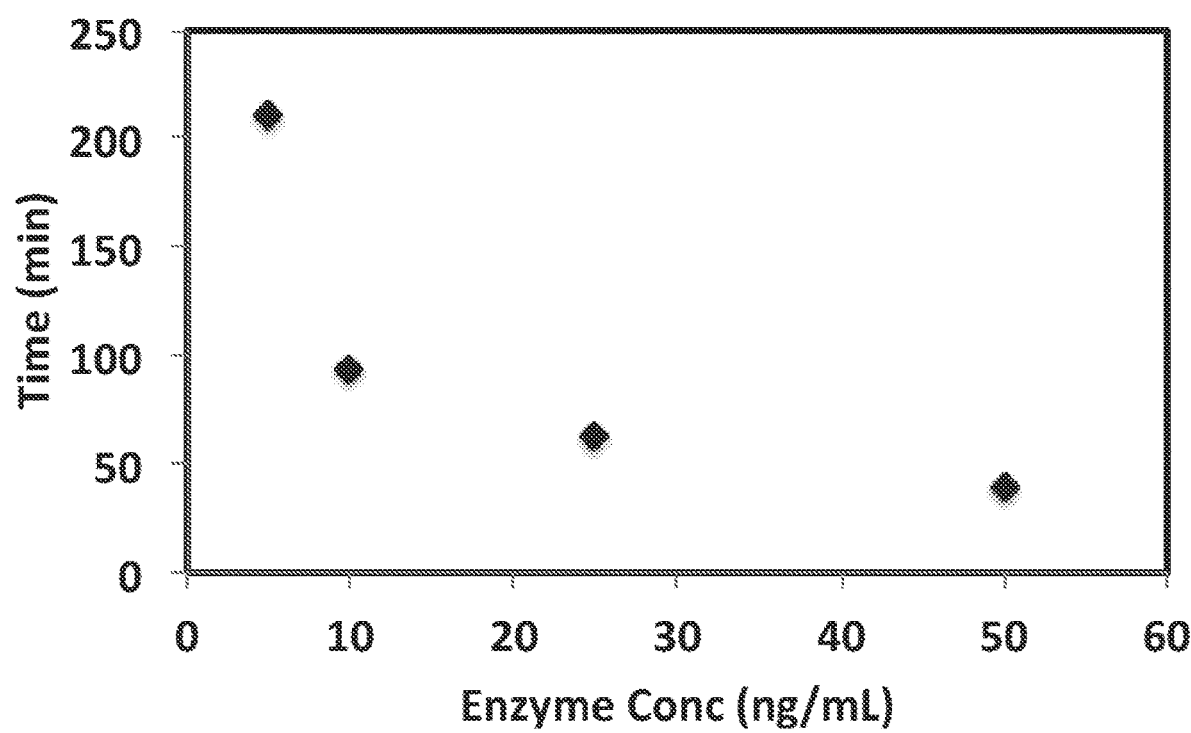
FIG. 19 shows aggregation time of A4 solutions at 50 µM incubated at 40° C. with different concentrations of MMP-1. As the concentrations increases, the aggregation time decreases.

The change in transition temperature shows the effect of cleaving the MMP-1 substrate. We also showed that addition of MMP-1 to these biopolymer solutions while keeping them just above their transition temperature produced a solution that became cloudy at different times depending on the enzyme concentration (FIG. 18). Accordingly, aggregation time can be used to estimate the enzyme concentration in an unknown solution. FIG. 19 shows a calibration curve for one such biopolymer at a constant temperature and various concentrations of MMP-1 enzyme.

Example 5

The present example demonstrates the use of non-protease enzymatic modifications of peptides to induce changes in environmentally-responsive polymers and biopolymers. Protein arginine deiminases (PADs) are calcium-dependent enzymes that catalyze the conversion of peptidyl-arginine into peptidyl-citrulline. This is a post-translational modification that results in loss of charges on arginine. Particularly, up-regulation of protein arginine deiminase 4 (PAD4) in the synovium of rheumatoid arthritis (RA) patients is thought to lead to the production of autoantibodies against modified proteins and subsequent articulation inflammation.

In the present example, an elastin-like-polypeptide (ELP) was fused to a substrate peptide for PAD4. Addition of PAD4 neutralizes the charge of arginine in the substrate peptide and decreases the transition temperature of the biopolymer due to its change in hydrophobicity. At a given temperature, the time for this transition to occur can then be correlated to the enzymatic activity of PAD4.

Figure 20:
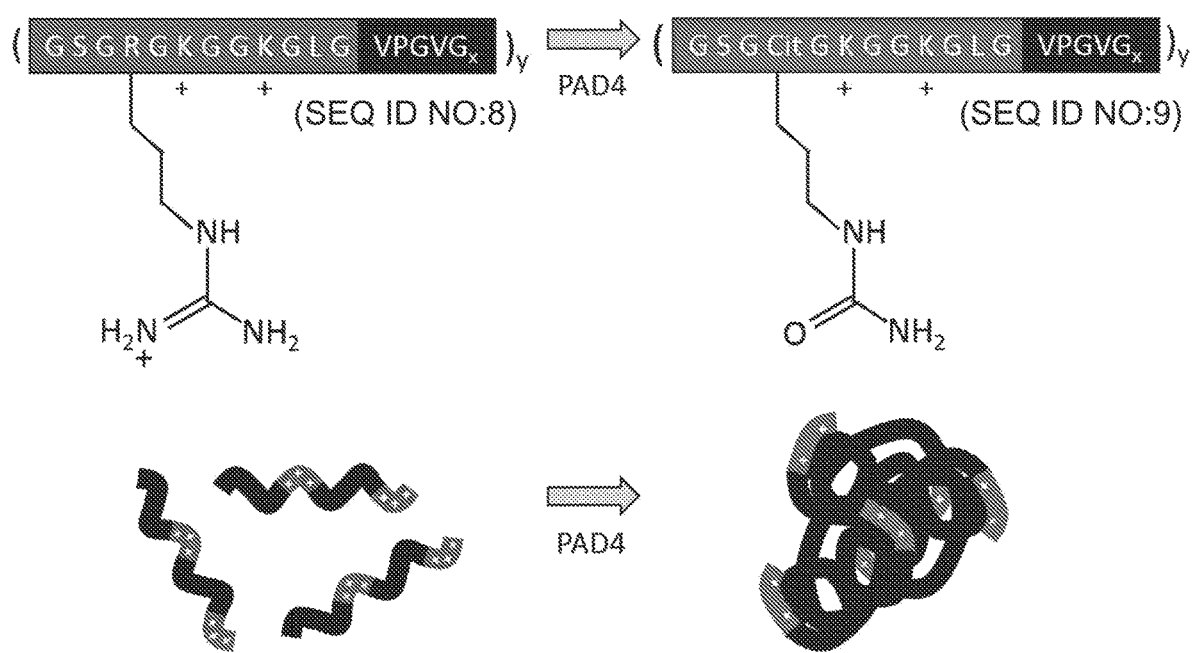
FIG. 20 shows a schematic diagram depicting a mechanism of aggregation of ELP-fusion construct in the presence of PAD4.
Figure 21:
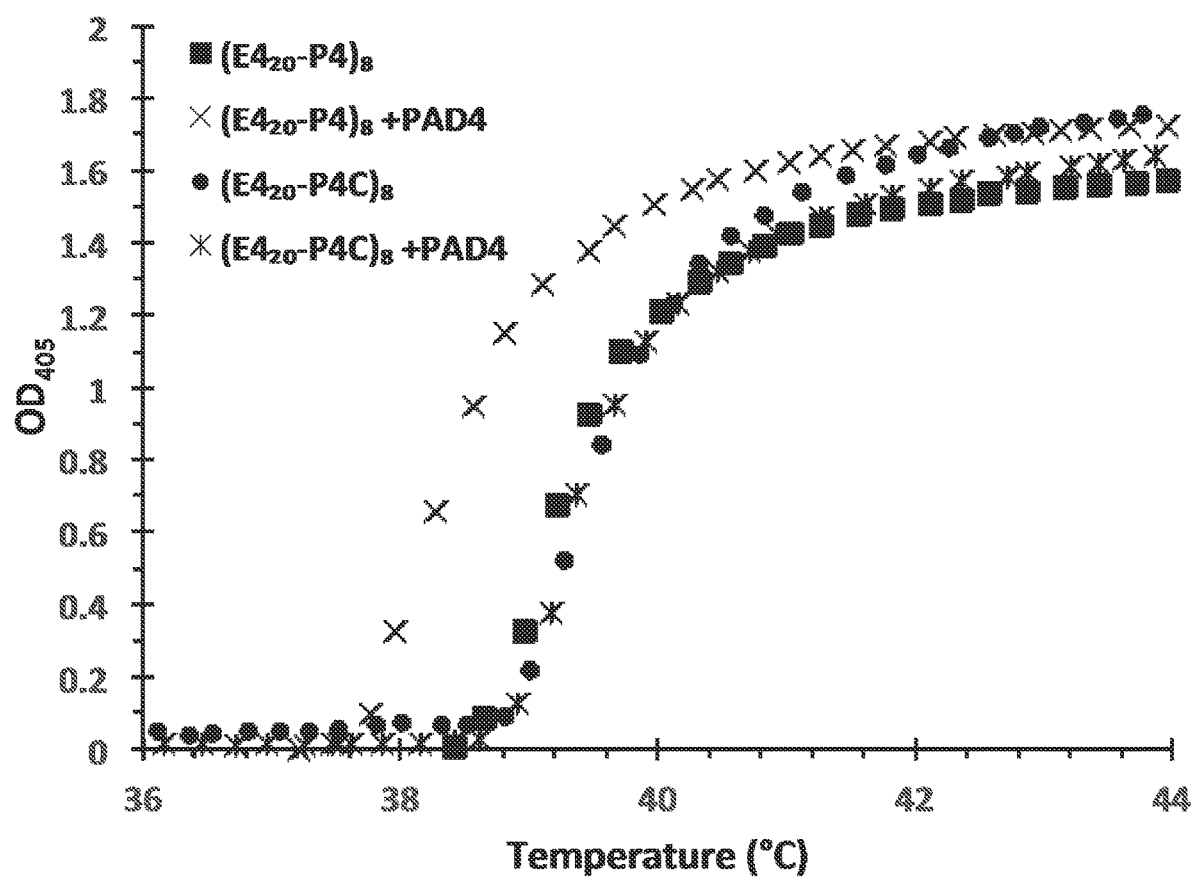
FIG. 21 shows transition temperature shifts of two ELP-fusion constructs in the presence of PAD4 enzyme.

For example, FIG. 20 shows a schematic diagram depicting the proposed mechanism of aggregation of an ELP-fusion construct in the presence of PAD4. FIG. 21 shows the transition temperature shifts of two ELP-fusion constructs in the presence of PAD4 enzyme. It is therefore possible to modify the presently disclosed modular molecular assay system to detect other peptide-modifying reactions (i.e., beyond simple cleavage) that result in changes in phase behavior. These changes can then be used to measure the activities of enzymes in solution that catalyze those changes in phase behavior.

Example 6

Figure 22B:
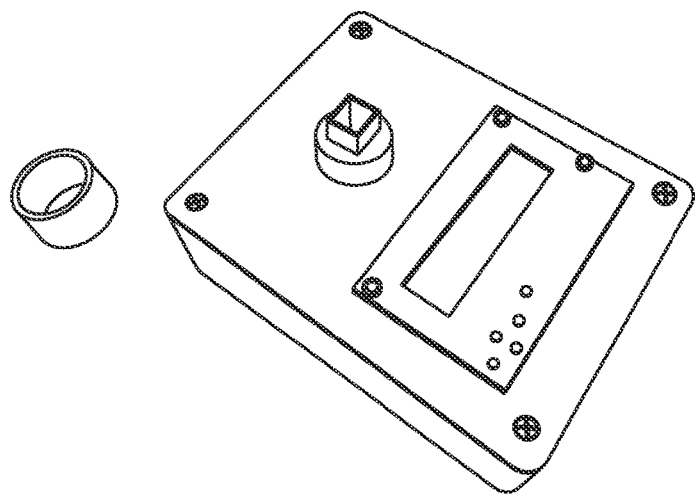

The present example provides a design for a portable, low cost detection device based on the presently disclosed modular assay system. A flowchart illustration of a design for one possible embodiment of the device is shown in FIG. 22A, and a photograph of such as a detection device is shown in FIG. 22B. The device operates as follows. The light from an LED lamp powered by a battery is shined on a sample. The intensity of light which passes through the sample is proportional to the turbidity of the sample. A photo-detector detects the light and converts the light into electrical output signal. Based on the intensity of the incoming light, the output signal changes. The output signal from the photo-detector is sent to a small micro-controller. The controller is programmed such that when the signal is above a certain threshold it starts a timer, and when it falls below a preset value it stops the timer. The resulting time is the "aggregation time" and is the output of the assay device.

What is claimed:

1. A method for detecting protease activity in a sample comprising
   a) contacting the sample with amphiphilic fusion polypeptides, wherein each of the fusion polypeptides comprise repeats of a hydrophobic domain of an elastin-like polypeptide having a lower critical solution temperature and repeats of a hydrophilic domain separated by a protease substrate domain;
   b) providing a stimulus in response to which the fusion polypeptides self-assemble into micelles comprising coronae comprising the protease substrate domains;
   c) providing conditions in which a protease present in the sample will cleave the protease substrate domain, whereby the hydrophobic domains of the micelles aggregate into particles at a detectable aggregation rate; and
   d) detecting the aggregation rate of the particles in the sample;
   wherein the aggregation rate of the particles in the sample is positively correlated to the protease activity in the sample.

2. The method of claim 1, wherein the protease substrate domains comprise a cleavage site for a protease selected from the group consisting of a serine protease, a threonine protease, a cysteine protease, an asparatic protease, a glutamic protease, and a metalloproteinase.

3. The method of claim 1, wherein detecting the aggregation rate of particles in the sample comprises optical turbidimetry.

4. The method of claim 1, wherein detecting the aggregation rate of particles in the sample comprises visual observation.

5. The method of claim 1 wherein the hydrophobic domain comprises repeats of the amino acid sequence GVGVP (SEQ ID NO: 23) or VPGVG (SEQ ID NO: 4).

6. The method of claim 5 wherein the hydrophobic domain comprises sixty (60) repeats of the amino acid sequence GVGVP (SEQ ID NO: 23) or VPGVG (SEQ ID NO: 4).

7. The method of claim 5 wherein the hydrophobic domain comprises sixty (60) repeats of the amino acid sequence GVGVP (SEQ ID NO: 23) or VPGVG (SEQ ID NO: 4).

8. The method of claim 1 wherein the hydrophilic domain comprises DEGQQDDEEGY (SEQ ID NO: 11) or repeats of VPGAGVPGGG (SEQ ID NO: 5).

9. The method of claim 1 wherein the hydrophilic domain comprises thirty (30) repeats of VPGAGVPGGG (SEQ. ID NO: 5).

10. The method of claim 1 wherein the hydrophilic domain is located at the C-terminal of the protease substrate domain.

11. The method of claim 1 wherein:
the hydrophobic domain comprises repeats of the amino acid sequence GVGVP (SEQ ID NO: 23) or VPGVG (SEQ ID NO: 4);
the hydrophilic domain comprises DEGQQDDEEGY (SEQ ID NO: 11) or repeats of VPGAGVPGGG (SEQ ID NO: 5); and
the hydrophilic domain is located at the C-terminal of the protease substrate domain.

12. The method of claim 11 wherein the hydrophobic domain comprises sixty (60) repeats of the amino acid sequence GVGVP (SEQ ID NO: 23) or VPGVG (SEQ ID NO: 4) and the hydrophilic domain comprises thirty (30) repeats of VPGAGVPGGG (SEQ ID NO: 5).

13. The method of claim 11 wherein the hydrophobic domain comprises sixty (60) repeats of the amino acid sequence GVGVP (SEQ ID NO: 23) or VPGVG (SEQ ID NO: 4) and the hydrophilic domain comprises thirty (30) repeats of VPGAGVPGGG (SEQ ID NO: 5).

14. The method of claim 1 wherein the hydrophilic domain comprises DEGQQDDEEGY (SEQ ID NO: 11) or repeats of VPGAGVPGGG (SEQ ID NO: 5).

15. The method of claim 1 wherein the hydrophilic domain comprises thirty (30) repeats of VPGAGVPGGG (SEQ ID NO: 5).

16. The method of claim 1 wherein the hydrophilic domain is located at the C-terminal of the protease substrate domain.

17. The method of claim 1 wherein:
the hydrophobic domain comprises repeats of the amino acid sequence GVGVP (SEQ ID NO: 23) or VPGVG (SEQ ID NO: 4);
the hydrophilic domain comprises DEGQQDDEEGY (SEQ ID NO: 11) or repeats of VPGAGVPGGG (SEQ ID NO: 5); and
the hydrophilic domain is located at the C-terminal of the protease substrate domain.

18. A method of predicting or diagnosing a disease in a subject comprising:
determining the activity of a protease in a biological sample of the subject using the method of claim 1 relative to the activity of the protease from a control sample from the subject or a control sample from subjects who do not have the disease;
wherein a significant difference between the activity of the protease in the biological sample and the control sample is indicative that the subject has or is susceptible to developing the disease.

19. The method of claim 18, wherein the disease is selected from the group consisting of an infectious disease, an inflammatory disease, a cardiovascular disease, and a cancer.

20. The method of claim 18, wherein the protease is a metalloproteinase.

21. The method of claim 18, wherein the protease is selected from the group consisting of a serine protease, a threonine protease, a cysteine protease, an asparatic protease, a glutamic protease, and a metalloproteinase.

22. The method of claim 18 wherein an increase in the activity of the protease is indicative of the disease.

23. A method of monitoring the progression or recurrence of a disease in a subject comprising:
determining the activity of a protease in a biological sample of the subject using the method of claim 1 relative to the activity of the protease from a control sample from the subject or a control sample from subjects who do not have the disease;
wherein a significant difference between the activity of the protease in the biological sample and the control sample is indicative of the progression or recurrence of the disease in the subject.

24. The method of claim 23, wherein the disease is selected from the group consisting of an infectious disease, an inflammatory disease, a cardiovascular disease, and a cancer.

25. The method of claim 23, wherein the protease is a metalloproteinase.

26. The method of claim 23, wherein the protease is selected from the group consisting of a serine protease, a threonine protease, a cysteine protease, an asparatic protease, a glutamic protease, and a metalloproteinase.

27. The method of claim 23 wherein an increase in the activity of the protease is indicative of the progression or recurrence of the disease.

28. A method for determining the efficacy of a therapeutic treatment for a disease in a subject undergoing the treatment comprising:
determining the activity of a protease in a biological sample of the subject subjected to therapeutic treatment using the method of claim 1 relative to the activity of the protease from a control sample from the subject or a control sample from subjects who do not have the disease;
wherein a significant difference between the activity of the protease in the biological sample and the control sample is indicative of the efficacy of the therapeutic treatment of the disease in the subject.

29. The method of claim 28, wherein the disease is selected from the group consisting of an infectious disease, an inflammatory disease, a cardiovascular disease, and a cancer.

30. The method of claim 28, wherein the protease is a metalloproteinase.

31. The method of claim 28, wherein the protease is selected from the group consisting of a serine protease, a threonine protease, a cysteine protease, an asparatic protease, a glutamic protease, and a metalloproteinase.

32. The method of claim 28 wherein a decrease in the activity of the protease is indicative of the efficacy of the therapeutic treatment.

33. A method of identifying an agent that inhibits the activity of a protease comprising:
a) detecting the activity of a protease in a sample using the method of claim 1;
b) contacting the sample with a candidate agent; and
c) comparing the activity of the protease in the sample after contact with the candidate agent to the activity of the protease in the sample before contact with the candidate agent;
wherein a significant decrease in the activity of the protease in the sample after contact with the candidate agent compared to the activity of the protease in the sample before contact with the candidate agent is indicative that the candidate agent is an agent that inhibits the activity of the protease.

34. The method of claim 33, wherein the protease is selected from the group consisting of a serine protease, a threonine protease, a cysteine protease, an asparatic protease, a glutamic protease, and a metalloproteinase.

35. A method for detecting protease activity in a sample comprising:
contacting the sample with amphiphilic fusion polypeptides, wherein each of the fusion polypeptides comprise:

a hydrophobic domain comprising sixty repeats of the amino acid sequence GVGVP (SEQ ID NO:23) or VPGVG (SEQ ID NO:4);
a hydrophilic domain comprising thirty repeats of DEGQQDDEEGY (SEQ ID NO:11) or VPGAGVPGGG (SEQ ID NO:5); and
a protease substrate domain separating the hydrophobic domain and the hydrophilic domain, wherein
the hydrophilic domain is located at the C-terminal of the protease substrate domain;
the fusion polypeptides self-assemble into micelles; and
the micelles comprise coronae comprising the protease substrate domains;
providing conditions in which a protease present in the sample will cleave the protease substrate domains, whereby the hydrophobic domains of the micelles aggregate into particles at a detectable aggregation rate; and
detecting the aggregation rate of the particles in the sample;
wherein the aggregation rate of particles in the sample is positively correlated to the protease activity in the sample.

36. A method for detecting protease activity in a sample, comprising:
contacting the sample with amphiphilic fusion polypeptides, wherein each of the fusion polypeptides comprise a hydrophobic domain comprising repeats of the amino acid sequence GVGVP (SEQ ID NO: 23) or VPGVG (SEQ ID NO: 4) and a hydrophilic domain separated by a protease substrate domain;
providing conditions in which the fusion polypeptides self-assemble into micelles comprising coronae comprising the protease substrate domains;
providing a temperature in which a protease present in the sample will cleave the protease substrate domains, whereby the hydrophobic domains of the micelles aggregate into particles at a detectable aggregation rate; and
detecting the aggregation rate of the particles in the sample;
wherein the aggregation rate of particles in the sample is positively correlated to the protease activity in the sample.

* * * * *

UNITED STATES PATENT AND TRADEMARK OFFICE
CERTIFICATE OF CORRECTION

| | | |
|---|---|---|
| PATENT NO. | : 11,268,127 B2 | Page 1 of 1 |
| APPLICATION NO. | : 15/116750 | |
| DATED | : March 8, 2022 | |
| INVENTOR(S) | : Lopez et al. | |

It is certified that error appears in the above-identified patent and that said Letters Patent is hereby corrected as shown below:

On the Title Page

In item (71), in "Applicants", in Column 1, Lines 1-6, delete "Applicants:Gabriel P. Lopez, Durham, NC (US); Ashutosh Chilkoti, Durham, NC (US); Ali Ghoorchian, Durham, NC (US); Felipe Garcia Quiroz, Durham, NC (US); Duke University, Durham, NC (US)" and insert --Applicant: Duke University, Durham, NC (US)-- therefor In the Claims In Column 43, Line 42, in Claim 1, after "comprising", insert --:--

Signed and Sealed this
Second Day of August, 2022

Katherine Kelly Vidal
*Director of the United States Patent and Trademark Office*